United States Patent
Levine et al.

(10) Patent No.: US 12,357,826 B2
(45) Date of Patent: Jul. 15, 2025

(54) EXTREMELY LOW DUTY-CYCLE ACTIVATION OF THE CHOLINERGIC ANTI-INFLAMMATORY PATHWAY TO TREAT CHRONIC INFLAMMATION

(71) Applicant: SetPoint Medical Corporation, Valencia, CA (US)

(72) Inventors: Jacob A. Levine, West Hempstead, NY (US); Michael A. Faltys, Valencia, CA (US)

(73) Assignee: SetPoint Medical Corporation, Valencia, CA (US)

( * ) Notice: Subject to any disclaimer, the term of this patent is extended or adjusted under 35 U.S.C. 154(b) by 0 days.

(21) Appl. No.: 15/853,350

(22) Filed: Dec. 22, 2017

(65) Prior Publication Data

US 2018/0117320 A1    May 3, 2018

Related U.S. Application Data

(63) Continuation of application No. 14/968,702, filed on Dec. 14, 2015, now Pat. No. 9,849,286, which is a continuation of application No. 14/336,942, filed on Jul. 21, 2014, now Pat. No. 9,211,410, which is a continuation-in-part of application No. 13/467,928, filed on May 9, 2012, now Pat. No. 8,788,034.

(Continued)

(51) Int. Cl.
   A61N 1/00     (2006.01)
   A61N 1/36    (2006.01)
   A61N 1/372   (2006.01)

(52) U.S. Cl.
   CPC ..... *A61N 1/36053* (2013.01); *A61N 1/36139* (2013.01); *A61N 1/36167* (2013.01); *A61N 1/36175* (2013.01); *A61N 1/37205* (2013.01)

(58) Field of Classification Search
   CPC .......... A61N 1/36053; A61N 1/36128–36178; A61N 1/37205; A61N 1/36139; A61N 1/36167; A61N 1/36175; A61N 1/36031
   See application file for complete search history.

(56) References Cited

U.S. PATENT DOCUMENTS

| | | |
|---|---|---|
| 2,164,121 A | 6/1939 | Pescador |
| 3,363,623 A | 1/1968 | Atwell |

(Continued)

FOREIGN PATENT DOCUMENTS

| | | |
|---|---|---|
| CN | 201230913 A | 5/2009 |
| CN | 101528303 A | 9/2009 |

(Continued)

OTHER PUBLICATIONS

US 6,184,239 B1, 02/2001, Puskas (withdrawn)

(Continued)

*Primary Examiner* — Scott M. Getzow
(74) *Attorney, Agent, or Firm* — Shay Glenn LLP

(57) ABSTRACT

Described herein are systems and methods for applying extremely low duty-cycle stimulation sufficient to treat chronic inflammation using feedback to adjust the off times between stimulations. In particular, the feedback include an assessment of the level of inflammation by the patient or the healthcare provider, or by measure the level of an inflammatory analyte or biomarker, or by detecting nerve activity correlated with inflammation.

21 Claims, 6 Drawing Sheets

Related U.S. Application Data

(60) Provisional application No. 61/484,112, filed on May 9, 2011.

(56) References Cited

U.S. PATENT DOCUMENTS

| | | |
|---|---|---|
| 3,631,534 A | 12/1971 | Hirota et al. |
| 4,073,296 A | 2/1978 | McCall |
| 4,098,277 A | 7/1978 | Mendell |
| 4,305,402 A | 12/1981 | Katims |
| 4,503,863 A | 3/1985 | Katims |
| 4,573,481 A | 3/1986 | Bullara |
| 4,590,946 A | 5/1986 | Loeb |
| 4,632,095 A | 12/1986 | Libin |
| 4,649,936 A | 3/1987 | Ungar et al. |
| 4,702,254 A | 10/1987 | Zabara |
| 4,840,793 A | 6/1989 | Todd, III et al. |
| 4,867,164 A | 9/1989 | Zabara |
| 4,929,734 A | 5/1990 | Coughenour et al. |
| 4,930,516 A | 6/1990 | Alfano et al. |
| 4,935,234 A | 6/1990 | Todd, III et al. |
| 4,979,511 A | 12/1990 | Terry, Jr. |
| 4,991,578 A | 2/1991 | Cohen |
| 5,019,648 A | 5/1991 | Schlossman et al. |
| 5,025,807 A | 6/1991 | Zabara |
| 5,038,781 A | 8/1991 | Lynch |
| 5,049,659 A | 9/1991 | Cantor et al. |
| 5,073,560 A | 12/1991 | Wu et al. |
| 5,106,853 A | 4/1992 | Showell et al. |
| 5,111,815 A | 5/1992 | Mower |
| 5,154,172 A | 10/1992 | Terry, Jr. et al. |
| 5,175,166 A | 12/1992 | Dunbar et al. |
| 5,179,950 A | 1/1993 | Stanislaw |
| 5,186,170 A | 2/1993 | Varrichio et al. |
| 5,188,104 A | 2/1993 | Wernicke et al. |
| 5,203,326 A | 4/1993 | Collins |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker et al. |
| 5,251,634 A | 10/1993 | Weinberg |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,330,507 A | 7/1994 | Schwartz |
| 5,330,515 A | 7/1994 | Rutecki et al. |
| 5,335,657 A | 8/1994 | Terry, Jr. et al. |
| 5,344,438 A | 9/1994 | Testerman et al. |
| 5,351,394 A | 10/1994 | Weinberg |
| 5,403,845 A | 4/1995 | Dunbar et al. |
| 5,458,625 A | 10/1995 | Kendall |
| 5,472,841 A | 12/1995 | Jayasena et al. |
| 5,487,756 A | 1/1996 | Kallesoe et al. |
| 5,496,938 A | 3/1996 | Gold et al. |
| 5,503,978 A | 4/1996 | Schneider et al. |
| 5,531,778 A | 7/1996 | Maschino et al. |
| 5,540,730 A | 7/1996 | Terry, Jr. et al. |
| 5,540,734 A | 7/1996 | Zabara |
| 5,567,588 A | 10/1996 | Gold et al. |
| 5,567,724 A | 10/1996 | Kelleher et al. |
| 5,571,150 A | 11/1996 | Wernicke et al. |
| 5,580,737 A | 12/1996 | Polisky et al. |
| 5,582,981 A | 12/1996 | Toole et al. |
| 5,604,231 A | 2/1997 | Smith et al. |
| 5,607,459 A | 3/1997 | Paul et al. |
| 5,611,350 A | 3/1997 | John |
| 5,618,818 A | 4/1997 | Ojo et al. |
| 5,629,285 A | 5/1997 | Black et al. |
| 5,637,459 A | 6/1997 | Burke et al. |
| 5,651,378 A | 7/1997 | Matheny et al. |
| 5,654,151 A | 8/1997 | Allen et al. |
| 5,683,867 A | 11/1997 | Biesecker et al. |
| 5,690,681 A | 11/1997 | Geddes et al. |
| 5,690,693 A | 11/1997 | Wang et al. |
| 5,700,282 A | 12/1997 | Zabara |
| 5,705,337 A | 1/1998 | Gold et al. |
| 5,707,400 A | 1/1998 | Terry, Jr. et al. |
| 5,709,853 A | 1/1998 | Lino et al. |
| 5,712,375 A | 1/1998 | Jensen et al. |
| 5,718,912 A | 2/1998 | Thompson et al. |
| 5,726,017 A | 3/1998 | Lochrie et al. |
| 5,726,179 A | 3/1998 | Messer, Jr. et al. |
| 5,727,556 A | 3/1998 | Weth et al. |
| 5,733,255 A | 3/1998 | Dinh et al. |
| 5,741,802 A | 4/1998 | Kem et al. |
| 5,773,598 A | 6/1998 | Burke et al. |
| 5,786,462 A | 7/1998 | Schneider et al. |
| 5,788,656 A | 8/1998 | Mino |
| 5,792,210 A | 8/1998 | Wamubu et al. |
| 5,824,027 A | 10/1998 | Hoffer et al. |
| 5,853,005 A | 12/1998 | Scanlon |
| 5,854,289 A | 12/1998 | Bianchi et al. |
| 5,902,814 A | 5/1999 | Gordon et al. |
| 5,913,876 A | 6/1999 | Taylor et al. |
| 5,916,239 A | 6/1999 | Geddes et al. |
| 5,919,216 A | 7/1999 | Houben et al. |
| 5,928,272 A | 7/1999 | Adkins et al. |
| 5,964,794 A | 10/1999 | Bolz et al. |
| 5,977,144 A | 11/1999 | Meyer et al. |
| 5,994,330 A | 11/1999 | El Khoury |
| 6,002,964 A | 12/1999 | Feler et al. |
| 6,006,134 A | 12/1999 | Hill et al. |
| 6,017,891 A | 1/2000 | Eibl et al. |
| 6,028,186 A | 2/2000 | Tasset et al. |
| 6,051,017 A | 4/2000 | Loeb et al. |
| 6,083,696 A | 7/2000 | Biesecker et al. |
| 6,083,905 A | 7/2000 | Voorberg et al. |
| 6,096,728 A | 8/2000 | Collins et al. |
| 6,104,956 A | 8/2000 | Naritoku et al. |
| 6,110,900 A | 8/2000 | Gold et al. |
| 6,110,914 A | 8/2000 | Phillips et al. |
| 6,117,837 A | 9/2000 | Tracey et al. |
| 6,124,449 A | 9/2000 | Gold et al. |
| 6,127,119 A | 10/2000 | Stephens et al. |
| 6,140,490 A | 10/2000 | Biesecker et al. |
| 6,141,590 A | 10/2000 | Reniric et al. |
| 6,147,204 A | 11/2000 | Gold et al. |
| 6,159,145 A | 12/2000 | Satoh |
| 6,164,284 A | 12/2000 | Schulman et al. |
| 6,166,048 A | 12/2000 | Bencherif |
| 6,168,778 B1 | 1/2001 | Janjic et al. |
| 6,171,795 B1 | 1/2001 | Korman et al. |
| 6,205,359 B1 | 3/2001 | Boveja |
| 6,208,894 B1 | 3/2001 | Schulman et al. |
| 6,208,902 B1 | 3/2001 | Boveja |
| 6,210,321 B1 | 4/2001 | Di Mino et al. |
| 6,224,862 B1 | 5/2001 | Turecek et al. |
| 6,233,488 B1 | 5/2001 | Hess |
| 6,266,564 B1 | 7/2001 | Hill et al. |
| 6,269,270 B1 | 7/2001 | Boveja |
| 6,304,775 B1 | 10/2001 | Iasemidis et al. |
| 6,308,104 B1 | 10/2001 | Taylor et al. |
| 6,337,997 B1 | 1/2002 | Rise |
| 6,339,725 B1 | 1/2002 | Naritoku et al. |
| 6,341,236 B1 | 1/2002 | Osorio et al. |
| 6,356,787 B1 | 3/2002 | Rezai et al. |
| 6,356,788 B2 | 3/2002 | Boveja |
| 6,381,499 B1 | 4/2002 | Taylor et al. |
| 6,405,732 B1 | 6/2002 | Edwards et al. |
| 6,407,095 B1 | 6/2002 | Lochead et al. |
| 6,428,484 B1 | 8/2002 | Battmer et al. |
| 6,429,217 B1 | 8/2002 | Puskas |
| 6,447,443 B1 | 9/2002 | Keogh et al. |
| 6,449,507 B1 | 9/2002 | Hill et al. |
| 6,473,644 B1 | 10/2002 | Terry, Jr. et al. |
| 6,479,523 B1 | 11/2002 | Puskas |
| 6,487,446 B1 | 11/2002 | Hill et al. |
| 6,511,500 B1 | 1/2003 | Rahme |
| 6,528,529 B1 | 3/2003 | Brann et al. |
| 6,532,388 B1 | 3/2003 | Hill et al. |
| 6,542,774 B2 | 4/2003 | Hill et al. |

(56) References Cited

U.S. PATENT DOCUMENTS

| | | | |
|---|---|---|---|
| 6,556,868 B2 | 4/2003 | Naritoku et al. |
| 6,564,102 B1 | 5/2003 | Boveja |
| 6,587,719 B1 | 7/2003 | Barrett et al. |
| 6,587,727 B2 | 7/2003 | Osorio et al. |
| 6,600,956 B2 | 7/2003 | Maschino et al. |
| 6,602,891 B2 | 8/2003 | Messer et al. |
| 6,609,025 B2 | 8/2003 | Barrett et al. |
| 6,610,713 B2 | 8/2003 | Tracey |
| 6,611,715 B1 | 8/2003 | Boveja |
| 6,615,081 B1 | 9/2003 | Boveja |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |
| 6,633,779 B1 | 10/2003 | Schuler et al. |
| 6,656,960 B2 | 12/2003 | Puskas |
| 6,668,191 B1 | 12/2003 | Boveja |
| 6,671,556 B2 | 12/2003 | Osorio et al. |
| 6,684,105 B2 | 1/2004 | Cohen et al. |
| 6,690,973 B2 | 2/2004 | Hill et al. |
| 6,718,208 B2 | 4/2004 | Hill et al. |
| 6,721,603 B2 | 4/2004 | Zabara et al. |
| 6,735,471 B2 | 5/2004 | Hill et al. |
| 6,735,474 B1 | 5/2004 | Loeb et al. |
| 6,735,475 B1 | 5/2004 | Whitehurst et al. |
| 6,760,626 B1 | 7/2004 | Boveja |
| 6,778,854 B2 | 8/2004 | Puskas |
| 6,804,558 B2 | 10/2004 | Haller et al. |
| RE38,654 E | 11/2004 | Hill et al. |
| 6,826,428 B1 | 11/2004 | Chen et al. |
| 6,832,114 B1 | 12/2004 | Whitehurst et al. |
| 6,838,471 B2 | 1/2005 | Tracey |
| RE38,705 E | 2/2005 | Hill et al. |
| 6,879,859 B1 | 4/2005 | Boveja |
| 6,885,888 B2 | 4/2005 | Rezai |
| 6,901,294 B1 | 5/2005 | Whitehurst et al. |
| 6,904,318 B2 | 6/2005 | Hill et al. |
| 6,920,357 B2 | 7/2005 | Osorio et al. |
| 6,928,320 B2 | 8/2005 | King |
| 6,934,583 B2 | 8/2005 | Weinberg et al. |
| 6,937,903 B2 | 8/2005 | Schuler et al. |
| 6,961,618 B2 | 11/2005 | Osorio et al. |
| 6,978,787 B1 | 12/2005 | Broniatowski |
| 7,011,638 B2 | 3/2006 | Schuler et al. |
| 7,054,686 B2 | 5/2006 | MacDonald |
| 7,054,692 B1* | 5/2006 | Whitehurst | A61N 1/37518 607/149 |
| 7,058,447 B2 | 6/2006 | Hill et al. |
| 7,062,320 B2 | 6/2006 | Ehlinger, Jr. |
| 7,069,082 B2 | 6/2006 | Lindenthaler |
| 7,072,720 B2 | 7/2006 | Puskas |
| 7,076,307 B2 | 7/2006 | Boveja et al. |
| 7,142,910 B2 | 11/2006 | Puskas |
| 7,142,917 B2 | 11/2006 | Fukui |
| 7,149,574 B2 | 12/2006 | Yun et al. |
| 7,155,279 B2 | 12/2006 | Whitehurst et al. |
| 7,155,284 B1 | 12/2006 | Whitehurst et al. |
| 7,167,750 B2 | 1/2007 | Knudson et al. |
| 7,167,751 B1* | 1/2007 | Whitehurst | A61N 1/3605 607/40 |
| 7,174,218 B1 | 2/2007 | Kuzma |
| 7,184,828 B2 | 2/2007 | Hill et al. |
| 7,184,829 B2 | 2/2007 | Hill et al. |
| 7,191,012 B2 | 3/2007 | Boveja et al. |
| 7,204,815 B2 | 4/2007 | Connor |
| 7,209,787 B2 | 4/2007 | DiLorenzo |
| 7,225,019 B2 | 5/2007 | Jahns et al. |
| 7,228,167 B2 | 6/2007 | Kara et al. |
| 7,238,715 B2 | 7/2007 | Tracey et al. |
| 7,242,984 B2 | 7/2007 | DiLorenzo |
| 7,269,457 B2 | 9/2007 | Shafer et al. |
| 7,345,178 B2 | 3/2008 | Nunes et al. |
| 7,373,204 B2 | 5/2008 | Gelfand et al. |
| 7,389,145 B2 | 6/2008 | Kilgore et al. |
| 7,454,245 B2 | 11/2008 | Armstrong et al. |
| 7,467,016 B2 | 12/2008 | Colborn |
| 7,544,497 B2 | 6/2009 | Sinclair et al. |
| 7,561,918 B2 | 7/2009 | Armstrong et al. |
| 7,634,315 B2 | 12/2009 | Cholette |
| 7,711,432 B2 | 5/2010 | Thimineur et al. |
| 7,729,760 B2 | 6/2010 | Patel et al. |
| 7,751,891 B2 | 7/2010 | Armstrong et al. |
| 7,776,326 B2 | 8/2010 | Milbrandt et al. |
| 7,797,058 B2 | 9/2010 | Mrva et al. |
| 7,819,883 B2 | 10/2010 | Westlund et al. |
| 7,822,486 B2 | 10/2010 | Foster et al. |
| 7,829,556 B2 | 11/2010 | Bemis et al. |
| 7,869,869 B1 | 1/2011 | Farazi |
| 7,869,885 B2 | 1/2011 | Begnaud et al. |
| 7,937,145 B2 | 5/2011 | Dobak |
| 7,962,220 B2 | 6/2011 | Kolafa et al. |
| 7,974,701 B2 | 7/2011 | Armstrong |
| 7,974,707 B2 | 7/2011 | Inman |
| 7,996,088 B2 | 8/2011 | Marrosu et al. |
| 7,996,092 B2 | 8/2011 | Mrva et al. |
| 8,019,419 B1 | 9/2011 | Panescu et al. |
| 8,060,208 B2 | 11/2011 | Kilgore et al. |
| 8,103,349 B2 | 1/2012 | Donders et al. |
| 8,165,668 B2 | 4/2012 | Dacey, Jr. et al. |
| 8,180,446 B2 | 5/2012 | Dacey, Jr. et al. |
| 8,180,447 B2 | 5/2012 | Dacey et al. |
| 8,195,287 B2 | 6/2012 | Dacey, Jr. et al. |
| 8,214,056 B2 | 7/2012 | Hoffer et al. |
| 8,233,982 B2 | 7/2012 | Libbus |
| 8,391,970 B2 | 3/2013 | Tracey et al. |
| 8,412,338 B2 | 4/2013 | Faltys |
| 8,504,161 B1* | 8/2013 | Kornet | A61N 1/36053 607/2 |
| 8,571,654 B2 | 10/2013 | Libbus et al. |
| 8,577,458 B1 | 11/2013 | Libbus et al. |
| 8,600,505 B2 | 12/2013 | Libbus et al. |
| 8,612,002 B2 | 12/2013 | Faltys et al. |
| 8,630,709 B2 | 1/2014 | Libbus et al. |
| 8,688,212 B2 | 4/2014 | Libbus et al. |
| 8,700,150 B2 | 4/2014 | Libbus et al. |
| 8,729,129 B2 | 5/2014 | Tracey et al. |
| 8,788,034 B2 | 7/2014 | Levine et al. |
| 8,843,210 B2 | 9/2014 | Simon et al. |
| 8,855,767 B2 | 10/2014 | Faltys et al. |
| 8,886,339 B2 | 11/2014 | Faltys et al. |
| 8,914,114 B2 | 12/2014 | Tracey et al. |
| 8,918,178 B2 | 12/2014 | Simon et al. |
| 8,918,191 B2 | 12/2014 | Libbus et al. |
| 8,923,964 B2 | 12/2014 | Libbus et al. |
| 8,983,628 B2 | 3/2015 | Simon et al. |
| 8,983,629 B2 | 3/2015 | Simon et al. |
| 8,996,116 B2 | 3/2015 | Faltys et al. |
| 9,114,262 B2 | 8/2015 | Libbus et al. |
| 9,162,064 B2 | 10/2015 | Faltys et al. |
| 9,174,041 B2 | 11/2015 | Faltys et al. |
| 9,211,409 B2 | 12/2015 | Tracey et al. |
| 9,211,410 B2 | 12/2015 | Levine et al. |
| 9,254,383 B2 | 2/2016 | Simon et al. |
| 9,272,143 B2 | 3/2016 | Libbus et al. |
| 9,358,381 B2 | 6/2016 | Simon et al. |
| 9,399,134 B2 | 7/2016 | Simon et al. |
| 9,403,001 B2 | 8/2016 | Simon et al. |
| 9,409,024 B2 | 8/2016 | KenKnight et al. |
| 9,415,224 B2 | 8/2016 | Libbus et al. |
| 9,452,290 B2 | 9/2016 | Libbus et al. |
| 9,511,228 B2 | 12/2016 | Amurthur et al. |
| 9,572,983 B2 | 2/2017 | Levine et al. |
| 9,662,490 B2 | 5/2017 | Tracey et al. |
| 9,700,716 B2 | 7/2017 | Faltys et al. |
| 9,833,621 B2 | 12/2017 | Levine |
| 9,849,286 B2 | 12/2017 | Levine et al. |
| 2001/0002441 A1 | 5/2001 | Boveja |
| 2001/0034542 A1* | 10/2001 | Mann | A61N 1/36164 607/30 |
| 2002/0026141 A1 | 2/2002 | Houben et al. |
| 2002/0040035 A1 | 4/2002 | Myers et al. |
| 2002/0077675 A1 | 6/2002 | Greenstein |
| 2002/0086871 A1 | 7/2002 | O'Neill et al. |

(56) References Cited

U.S. PATENT DOCUMENTS

| | | |
|---|---|---|
| 2002/0095139 A1 | 7/2002 | Keogh et al. |
| 2002/0099417 A1 | 7/2002 | Naritoku et al. |
| 2002/0138075 A1 | 9/2002 | Edwards et al. |
| 2002/0138109 A1 | 9/2002 | Keogh et al. |
| 2002/0193859 A1 | 12/2002 | Schulman et al. |
| 2002/0198570 A1 | 12/2002 | Puskas |
| 2003/0018367 A1 | 1/2003 | DiLorenzo |
| 2003/0032852 A1 | 2/2003 | Perreault et al. |
| 2003/0045909 A1 | 3/2003 | Gross et al. |
| 2003/0088301 A1 | 5/2003 | King |
| 2003/0191404 A1 | 10/2003 | Klein |
| 2003/0194752 A1 | 10/2003 | Anderson et al. |
| 2003/0195578 A1 | 10/2003 | Perron et al. |
| 2003/0212440 A1 | 11/2003 | Boveja |
| 2003/0229380 A1 | 12/2003 | Adams et al. |
| 2003/0236557 A1 | 12/2003 | Whitehurst et al. |
| 2003/0236558 A1 | 12/2003 | Whitehurst et al. |
| 2004/0002546 A1 | 1/2004 | Altschuler |
| 2004/0015202 A1 | 1/2004 | Chandler et al. |
| 2004/0015204 A1* | 1/2004 | Whitehurst ........ A61N 1/37252 607/48 |
| 2004/0015205 A1 | 1/2004 | Whitehurst et al. |
| 2004/0024422 A1 | 2/2004 | Hill et al. |
| 2004/0024428 A1 | 2/2004 | Barrett et al. |
| 2004/0024439 A1 | 2/2004 | Riso |
| 2004/0030362 A1 | 2/2004 | Hill et al. |
| 2004/0039427 A1 | 2/2004 | Barrett et al. |
| 2004/0048795 A1 | 3/2004 | Ivanova et al. |
| 2004/0049121 A1 | 3/2004 | Yaron |
| 2004/0049240 A1 | 3/2004 | Gerber et al. |
| 2004/0059383 A1 | 3/2004 | Puskas |
| 2004/0111139 A1 | 6/2004 | McCreery et al. |
| 2004/0138517 A1 | 7/2004 | Osorio et al. |
| 2004/0138518 A1 | 7/2004 | Rise et al. |
| 2004/0138536 A1 | 7/2004 | Frei et al. |
| 2004/0146949 A1 | 7/2004 | Tan et al. |
| 2004/0153127 A1 | 8/2004 | Gordon et al. |
| 2004/0158119 A1 | 8/2004 | Osorio et al. |
| 2004/0162584 A1 | 8/2004 | Hill et al. |
| 2004/0172074 A1 | 9/2004 | Yoshihito |
| 2004/0172085 A1 | 9/2004 | Knudson et al. |
| 2004/0172086 A1 | 9/2004 | Knudson et al. |
| 2004/0172088 A1 | 9/2004 | Knudson et al. |
| 2004/0172094 A1 | 9/2004 | Cohen et al. |
| 2004/0176812 A1 | 9/2004 | Knudson et al. |
| 2004/0178706 A1 | 9/2004 | D'Orso |
| 2004/0193231 A1 | 9/2004 | David et al. |
| 2004/0199209 A1 | 10/2004 | Hill et al. |
| 2004/0199210 A1 | 10/2004 | Shelchuk |
| 2004/0204355 A1 | 10/2004 | Tracey et al. |
| 2004/0215272 A1 | 10/2004 | Haubrich et al. |
| 2004/0215287 A1 | 10/2004 | Swoyer et al. |
| 2004/0236381 A1 | 11/2004 | Dinsmoor et al. |
| 2004/0236382 A1 | 11/2004 | Dinsmoor et al. |
| 2004/0240691 A1 | 12/2004 | Grafenberg |
| 2004/0243182 A1 | 12/2004 | Cohen et al. |
| 2004/0243211 A1 | 12/2004 | Colliou et al. |
| 2004/0254612 A1 | 12/2004 | Ezra et al. |
| 2004/0267152 A1 | 12/2004 | Pineda |
| 2005/0021092 A1 | 1/2005 | Yun et al. |
| 2005/0021101 A1 | 1/2005 | Chen et al. |
| 2005/0027328 A1 | 2/2005 | Greenstein |
| 2005/0043774 A1 | 2/2005 | Devlin et al. |
| 2005/0049655 A1 | 3/2005 | Boveja et al. |
| 2005/0065553 A1 | 3/2005 | Ben Ezra et al. |
| 2005/0065573 A1 | 3/2005 | Rezai |
| 2005/0065575 A1 | 3/2005 | Dobak |
| 2005/0070970 A1 | 3/2005 | Knudson et al. |
| 2005/0070974 A1 | 3/2005 | Knudson et al. |
| 2005/0075694 A1 | 4/2005 | Schmeling et al. |
| 2005/0075698 A1 | 4/2005 | Phillips et al. |
| 2005/0075701 A1 | 4/2005 | Shafer |
| 2005/0075702 A1 | 4/2005 | Shafer |
| 2005/0095246 A1 | 5/2005 | Shafer |
| 2005/0096707 A1 | 5/2005 | Hill et al. |
| 2005/0103351 A1 | 5/2005 | Stomberg et al. |
| 2005/0113894 A1 | 5/2005 | Zilberman et al. |
| 2005/0131467 A1 | 6/2005 | Boveja |
| 2005/0131486 A1 | 6/2005 | Boveja et al. |
| 2005/0131487 A1 | 6/2005 | Boveja |
| 2005/0131493 A1 | 6/2005 | Boveja et al. |
| 2005/0137644 A1 | 6/2005 | Boveja et al. |
| 2005/0137645 A1 | 6/2005 | Voipio et al. |
| 2005/0143781 A1 | 6/2005 | Carbunaru et al. |
| 2005/0143787 A1 | 6/2005 | Boveja et al. |
| 2005/0149126 A1 | 7/2005 | Libbus |
| 2005/0149129 A1 | 7/2005 | Libbus et al. |
| 2005/0149131 A1 | 7/2005 | Libbus et al. |
| 2005/0153885 A1 | 7/2005 | Yun et al. |
| 2005/0154425 A1 | 7/2005 | Boveja et al. |
| 2005/0154426 A1 | 7/2005 | Boveja et al. |
| 2005/0165458 A1 | 7/2005 | Boveja et al. |
| 2005/0177200 A1 | 8/2005 | George et al. |
| 2005/0182288 A1 | 8/2005 | Zabara |
| 2005/0182467 A1 | 8/2005 | Hunter et al. |
| 2005/0187584 A1 | 8/2005 | Denker et al. |
| 2005/0187586 A1 | 8/2005 | David et al. |
| 2005/0187590 A1 | 8/2005 | Boveja et al. |
| 2005/0191661 A1 | 9/2005 | Gatanaga et al. |
| 2005/0192644 A1 | 9/2005 | Boveja et al. |
| 2005/0197600 A1 | 9/2005 | Schuler et al. |
| 2005/0197675 A1 | 9/2005 | David et al. |
| 2005/0197678 A1 | 9/2005 | Boveja et al. |
| 2005/0203501 A1 | 9/2005 | Aldrich et al. |
| 2005/0209654 A1 | 9/2005 | Boveja et al. |
| 2005/0216064 A1 | 9/2005 | Heruth et al. |
| 2005/0216070 A1 | 9/2005 | Boveja et al. |
| 2005/0216071 A1 | 9/2005 | Devlin et al. |
| 2005/0240229 A1 | 10/2005 | Whitehurst et al. |
| 2005/0240231 A1 | 10/2005 | Aldrich et al. |
| 2005/0240241 A1 | 10/2005 | Yun et al. |
| 2005/0240242 A1 | 10/2005 | DiLorenzo |
| 2005/0251220 A1 | 11/2005 | Barrett et al. |
| 2005/0251222 A1 | 11/2005 | Barrett et al. |
| 2005/0267542 A1 | 12/2005 | David et al. |
| 2005/0267547 A1 | 12/2005 | Knudson et al. |
| 2005/0277912 A1 | 12/2005 | John |
| 2005/0283198 A1 | 12/2005 | Haubrich et al. |
| 2006/0009815 A1 | 1/2006 | Boveja et al. |
| 2006/0015151 A1 | 1/2006 | Aldrich |
| 2006/0025828 A1 | 2/2006 | Armstrong et al. |
| 2006/0036293 A1 | 2/2006 | Whitehurst et al. |
| 2006/0052657 A9 | 3/2006 | Zabara |
| 2006/0052831 A1 | 3/2006 | Fukui |
| 2006/0052836 A1 | 3/2006 | Kim et al. |
| 2006/0058851 A1 | 3/2006 | Cigaina |
| 2006/0064137 A1 | 3/2006 | Stone |
| 2006/0064139 A1 | 3/2006 | Chung et al. |
| 2006/0074450 A1 | 4/2006 | Boveja et al. |
| 2006/0074473 A1 | 4/2006 | Gertner |
| 2006/0079936 A1 | 4/2006 | Boveja et al. |
| 2006/0085046 A1 | 4/2006 | Rezai et al. |
| 2006/0095081 A1 | 5/2006 | Zhou et al. |
| 2006/0095090 A1 | 5/2006 | De Ridder |
| 2006/0100668 A1 | 5/2006 | Ben-David et al. |
| 2006/0106755 A1 | 5/2006 | Stuhec |
| 2006/0111644 A1 | 5/2006 | Guttag et al. |
| 2006/0111754 A1 | 5/2006 | Rezai et al. |
| 2006/0111755 A1 | 5/2006 | Stone et al. |
| 2006/0116739 A1 | 6/2006 | Betser et al. |
| 2006/0122675 A1 | 6/2006 | Libbus et al. |
| 2006/0129202 A1 | 6/2006 | Kurokawa |
| 2006/0129202 A1 | 6/2006 | Armstrong |
| 2006/0135998 A1* | 6/2006 | Libbus ............... A61N 1/36053 607/2 |
| 2006/0136024 A1 | 6/2006 | Cohen et al. |
| 2006/0142802 A1 | 6/2006 | Armstrong |
| 2006/0142822 A1 | 6/2006 | Tulgar |
| 2006/0149337 A1 | 7/2006 | John |
| 2006/0155495 A1 | 7/2006 | Osorio et al. |
| 2006/0161216 A1 | 7/2006 | John et al. |
| 2006/0161217 A1 | 7/2006 | Jaax et al. |
| 2006/0167497 A1 | 7/2006 | Armstrong et al. |
| 2006/0167498 A1 | 7/2006 | DiLorenzo |

(56) References Cited

U.S. PATENT DOCUMENTS

| | | |
|---|---|---|
| 2006/0167501 A1 | 7/2006 | Ben-David et al. |
| 2006/0173493 A1 | 8/2006 | Armstrong et al. |
| 2006/0173508 A1 | 8/2006 | Stone et al. |
| 2006/0178691 A1 | 8/2006 | Binmoeller |
| 2006/0178703 A1 | 8/2006 | Huston et al. |
| 2006/0178706 A1 | 8/2006 | Lisogurski et al. |
| 2006/0190044 A1 | 8/2006 | Libbus et al. |
| 2006/0190053 A1 | 8/2006 | Dobak |
| 2006/0200208 A1 | 9/2006 | Terry, Jr. et al. |
| 2006/0200219 A1 | 9/2006 | Thrope et al. |
| 2006/0206155 A1 | 9/2006 | Ben-David et al. |
| 2006/0206158 A1 | 9/2006 | Wu et al. |
| 2006/0229677 A1 | 10/2006 | Moffitt et al. |
| 2006/0229681 A1 | 10/2006 | Fischell |
| 2006/0241697 A1 | 10/2006 | Libbus et al. |
| 2006/0241699 A1 | 10/2006 | Libbus et al. |
| 2006/0247719 A1 | 11/2006 | Maschino et al. |
| 2006/0247721 A1 | 11/2006 | Maschino et al. |
| 2006/0247722 A1 | 11/2006 | Maschino et al. |
| 2006/0259077 A1 | 11/2006 | Pardo et al. |
| 2006/0259084 A1 | 11/2006 | Zhang et al. |
| 2006/0259085 A1 | 11/2006 | Zhang et al. |
| 2006/0259107 A1 | 11/2006 | Caparso et al. |
| 2006/0271115 A1 | 11/2006 | Ben-Ezra et al. |
| 2006/0282121 A1 | 12/2006 | Payne et al. |
| 2006/0282131 A1 | 12/2006 | Caparso et al. |
| 2006/0282145 A1 | 12/2006 | Caparso et al. |
| 2006/0287678 A1 | 12/2006 | Shafer |
| 2006/0287679 A1 | 12/2006 | Stone |
| 2006/0292099 A1 | 12/2006 | Milburn et al. |
| 2006/0293720 A1 | 12/2006 | DiLorenzo |
| 2006/0293721 A1 | 12/2006 | Tarver et al. |
| 2006/0293723 A1 | 12/2006 | Whitehurst et al. |
| 2007/0016262 A1 | 1/2007 | Gross et al. |
| 2007/0016263 A1 | 1/2007 | Armstrong et al. |
| 2007/0021785 A1 | 1/2007 | Inman et al. |
| 2007/0021786 A1 | 1/2007 | Parnis et al. |
| 2007/0021814 A1 | 1/2007 | Inman et al. |
| 2007/0025608 A1 | 2/2007 | Armstrong |
| 2007/0027482 A1 | 2/2007 | Parnis et al. |
| 2007/0027483 A1 | 2/2007 | Maschino et al. |
| 2007/0027484 A1 | 2/2007 | Guzman et al. |
| 2007/0027486 A1 | 2/2007 | Armstrong |
| 2007/0027492 A1 | 2/2007 | Maschino et al. |
| 2007/0027496 A1 | 2/2007 | Parnis et al. |
| 2007/0027497 A1 | 2/2007 | Parnis |
| 2007/0027498 A1 | 2/2007 | Maschino et al. |
| 2007/0027499 A1 | 2/2007 | Maschino et al. |
| 2007/0027500 A1 | 2/2007 | Maschino et al. |
| 2007/0027504 A1 | 2/2007 | Barrett et al. |
| 2007/0055324 A1 | 3/2007 | Thompson et al. |
| 2007/0067004 A1 | 3/2007 | Boveja et al. |
| 2007/0083242 A1 | 4/2007 | Mazgalev et al. |
| 2007/0093434 A1 | 4/2007 | Rossetti et al. |
| 2007/0093870 A1 | 4/2007 | Maschino |
| 2007/0093875 A1 | 4/2007 | Chavan et al. |
| 2007/0100263 A1 | 5/2007 | Merfeld |
| 2007/0100377 A1 | 5/2007 | Armstrong et al. |
| 2007/0100378 A1 | 5/2007 | Maschino |
| 2007/0100380 A1 | 5/2007 | Fukui |
| 2007/0100392 A1 | 5/2007 | Maschino et al. |
| 2007/0106339 A1 | 5/2007 | Errico et al. |
| 2007/0112404 A1 | 5/2007 | Mann et al. |
| 2007/0118177 A1 | 5/2007 | Libbus et al. |
| 2007/0118178 A1 | 5/2007 | Fukui |
| 2007/0129767 A1 | 6/2007 | Wahlstrand |
| 2007/0129780 A1 | 6/2007 | Whitehurst et al. |
| 2007/0135846 A1 | 6/2007 | Knudson et al. |
| 2007/0135856 A1 | 6/2007 | Knudson et al. |
| 2007/0135857 A1 | 6/2007 | Knudson et al. |
| 2007/0135858 A1 | 6/2007 | Knudson et al. |
| 2007/0136098 A1 | 6/2007 | Smythe et al. |
| 2007/0142870 A1 | 6/2007 | Knudson et al. |
| 2007/0142871 A1 | 6/2007 | Libbus et al. |
| 2007/0142874 A1 | 6/2007 | John |
| 2007/0150006 A1 | 6/2007 | Libbus et al. |
| 2007/0150011 A1 | 6/2007 | Meyer et al. |
| 2007/0150021 A1 | 6/2007 | Chen et al. |
| 2007/0150027 A1 | 6/2007 | Rogers |
| 2007/0156180 A1 | 7/2007 | Jaax et al. |
| 2007/0198063 A1 | 8/2007 | Hunter et al. |
| 2007/0239243 A1 | 10/2007 | Moffitt et al. |
| 2007/0244522 A1 | 10/2007 | Overstreet |
| 2007/0250145 A1 | 10/2007 | Kraus et al. |
| 2007/0255320 A1 | 11/2007 | Inman et al. |
| 2007/0255333 A1 | 11/2007 | Giftakis |
| 2007/0255339 A1 | 11/2007 | Torgerson |
| 2008/0015659 A1 | 1/2008 | Zhang |
| 2008/0021517 A1 | 1/2008 | Dietrich |
| 2008/0021520 A1 | 1/2008 | Dietrich |
| 2008/0046055 A1 | 2/2008 | Durand et al. |
| 2008/0051852 A1 | 2/2008 | Dietrich et al. |
| 2008/0058871 A1 | 3/2008 | Libbus et al. |
| 2008/0103407 A1 | 5/2008 | Bolea et al. |
| 2008/0140138 A1 | 6/2008 | Ivanova et al. |
| 2008/0166348 A1 | 7/2008 | Kupper et al. |
| 2008/0183226 A1 | 7/2008 | Buras et al. |
| 2008/0183246 A1 | 7/2008 | Patel et al. |
| 2008/0195171 A1 | 8/2008 | Sharma |
| 2008/0208266 A1 | 8/2008 | Lesser et al. |
| 2008/0213331 A1 | 9/2008 | Gelfand et al. |
| 2008/0234780 A1 | 9/2008 | Smith |
| 2008/0234790 A1 | 9/2008 | Bayer et al. |
| 2008/0281197 A1 | 11/2008 | Wiley et al. |
| 2008/0281365 A1 | 11/2008 | Tweden et al. |
| 2008/0281372 A1 | 11/2008 | Libbus et al. |
| 2009/0012590 A1 | 1/2009 | Inman et al. |
| 2009/0048194 A1 | 2/2009 | Aerssens et al. |
| 2009/0076561 A1* | 3/2009 | Libbus .............. A61N 1/36117 607/11 |
| 2009/0082832 A1 | 3/2009 | Carbunaru et al. |
| 2009/0088821 A1 | 4/2009 | Abrahamson |
| 2009/0105782 A1 | 4/2009 | Mickle et al. |
| 2009/0112291 A1 | 4/2009 | Wahlstrand et al. |
| 2009/0123521 A1 | 5/2009 | Weber et al. |
| 2009/0125076 A1 | 5/2009 | Shuros et al. |
| 2009/0125079 A1 | 5/2009 | Armstrong et al. |
| 2009/0131995 A1 | 5/2009 | Sloan et al. |
| 2009/0143831 A1* | 6/2009 | Huston .............. A61N 1/36053 607/2 |
| 2009/0171405 A1 | 7/2009 | Craig |
| 2009/0177112 A1 | 7/2009 | Gharib et al. |
| 2009/0182388 A1 | 7/2009 | Von Arx et al. |
| 2009/0187231 A1 | 7/2009 | Errico et al. |
| 2009/0210042 A1 | 8/2009 | Kowalczewski |
| 2009/0248097 A1 | 10/2009 | Tracey et al. |
| 2009/0254143 A1 | 10/2009 | Tweden et al. |
| 2009/0275997 A1 | 11/2009 | Faltys et al. |
| 2009/0276019 A1 | 11/2009 | Perez et al. |
| 2009/0281593 A9 | 11/2009 | Errico et al. |
| 2009/0281594 A1 | 11/2009 | King et al. |
| 2009/0312817 A1 | 12/2009 | Hogle et al. |
| 2010/0003656 A1 | 1/2010 | Kilgard et al. |
| 2010/0010556 A1 | 1/2010 | Zhao et al. |
| 2010/0010571 A1 | 1/2010 | Skelton et al. |
| 2010/0010581 A1 | 1/2010 | Goetz et al. |
| 2010/0010603 A1 | 1/2010 | Ben-David et al. |
| 2010/0016746 A1 | 1/2010 | Hampton et al. |
| 2010/0042186 A1 | 2/2010 | Ben-David et al. |
| 2010/0063563 A1 | 3/2010 | Craig |
| 2010/0074934 A1 | 3/2010 | Hunter |
| 2010/0167937 A1 | 7/2010 | Goldknopf et al. |
| 2010/0191304 A1 | 7/2010 | Scott |
| 2010/0204766 A1* | 8/2010 | Zdeblick .............. A61N 1/025 607/119 |
| 2010/0215632 A1 | 8/2010 | Boss et al. |
| 2010/0219796 A1 | 9/2010 | Kallmyer |
| 2010/0241183 A1 | 9/2010 | DiLorenzo |
| 2010/0241195 A1* | 9/2010 | Meadows ............ A61N 1/3787 607/2 |
| 2010/0241207 A1 | 9/2010 | Bluger |
| 2010/0249859 A1 | 9/2010 | DiLorenzo |
| 2010/0280500 A1 | 11/2010 | Skelton et al. |
| 2010/0280562 A1 | 11/2010 | Pi et al. |

(56) References Cited

U.S. PATENT DOCUMENTS

| | | | |
|---|---|---|---|
| 2010/0280569 A1 | 11/2010 | Bobillier et al. | |
| 2010/0312320 A1* | 12/2010 | Faltys | A61N 1/36114 607/118 |
| 2011/0004266 A1 | 1/2011 | Sharma | |
| 2011/0009734 A1 | 1/2011 | Foley et al. | |
| 2011/0042574 A1 | 2/2011 | Nishino et al. | |
| 2011/0054569 A1 | 3/2011 | Zitnik et al. | |
| 2011/0066208 A1 | 3/2011 | Pasricha et al. | |
| 2011/0082515 A1 | 4/2011 | Libbus et al. | |
| 2011/0092882 A1 | 4/2011 | Firlik et al. | |
| 2011/0144717 A1 | 6/2011 | Burton et al. | |
| 2011/0145588 A1 | 6/2011 | Stubbs et al. | |
| 2011/0152967 A1 | 6/2011 | Simon et al. | |
| 2011/0190849 A1* | 8/2011 | Faltys | A61N 1/36053 607/50 |
| 2011/0224749 A1 | 9/2011 | Ben-David et al. | |
| 2011/0247620 A1 | 10/2011 | Armstrong et al. | |
| 2011/0275927 A1 | 11/2011 | Wagner et al. | |
| 2011/0301658 A1 | 12/2011 | Yoo et al. | |
| 2011/0301667 A1 | 12/2011 | Olson et al. | |
| 2011/0307027 A1 | 12/2011 | Sharma et al. | |
| 2012/0053657 A1 | 3/2012 | Parker et al. | |
| 2012/0065706 A1 | 3/2012 | Vallapureddy et al. | |
| 2012/0179219 A1 | 7/2012 | Kisker et al. | |
| 2012/0185009 A1 | 7/2012 | Kornet et al. | |
| 2012/0185020 A1 | 7/2012 | Simon et al. | |
| 2012/0296176 A1 | 11/2012 | Herbst | |
| 2012/0302821 A1 | 11/2012 | Burnett | |
| 2013/0013016 A1 | 1/2013 | Diebold | |
| 2013/0018439 A1 | 1/2013 | Chow et al. | |
| 2013/0066392 A1 | 3/2013 | Simon et al. | |
| 2013/0066395 A1 | 3/2013 | Simon et al. | |
| 2013/0150756 A1 | 6/2013 | Vitek et al. | |
| 2013/0245718 A1 | 9/2013 | Birkholz et al. | |
| 2013/0274831 A1 | 10/2013 | Otto et al. | |
| 2013/0278226 A1 | 10/2013 | Cong et al. | |
| 2013/0289385 A1 | 10/2013 | Lozano et al. | |
| 2013/0317580 A1 | 11/2013 | Simon et al. | |
| 2014/0046407 A1 | 2/2014 | Ben-Ezra et al. | |
| 2014/0070761 A1 | 3/2014 | Labbe et al. | |
| 2014/0105255 A1 | 4/2014 | Kutner | |
| 2014/0206945 A1 | 7/2014 | Liao | |
| 2014/0213926 A1 | 7/2014 | Vaidyanathan | |
| 2014/0257425 A1* | 9/2014 | Arcot-Krishnamurthy | A61N 1/36117 607/44 |
| 2014/0277260 A1 | 9/2014 | Khalil et al. | |
| 2014/0288551 A1 | 9/2014 | Bharmi et al. | |
| 2014/0324118 A1 | 10/2014 | Simon et al. | |
| 2014/0330335 A1 | 11/2014 | Errico et al. | |
| 2014/0371818 A1 | 12/2014 | Bond et al. | |
| 2015/0018728 A1 | 1/2015 | Gross et al. | |
| 2015/0100100 A1 | 4/2015 | Tracey et al. | |
| 2015/0119956 A1 | 4/2015 | Libbus et al. | |
| 2015/0133717 A1 | 5/2015 | Ghiron et al. | |
| 2015/0180271 A1 | 6/2015 | Angara et al. | |
| 2015/0196767 A1 | 7/2015 | Ahmed | |
| 2015/0202446 A1 | 7/2015 | Franke et al. | |
| 2015/0233904 A1 | 8/2015 | Nayak | |
| 2015/0241447 A1 | 8/2015 | Zitnik et al. | |
| 2016/0038745 A1 | 2/2016 | Faltys et al. | |
| 2016/0067497 A1 | 3/2016 | Levine et al. | |
| 2016/0114165 A1 | 4/2016 | Levine et al. | |
| 2016/0250097 A9 | 9/2016 | Tracey et al. | |
| 2016/0331952 A1 | 11/2016 | Faltys et al. | |
| 2016/0367808 A9 | 12/2016 | Simon et al. | |
| 2017/0113044 A1 | 4/2017 | Levine et al. | |
| 2017/0197076 A1 | 7/2017 | Faltys et al. | |
| 2017/0202467 A1 | 7/2017 | Zitnik et al. | |
| 2017/0203103 A1 | 7/2017 | Levine et al. | |
| 2017/0209705 A1 | 7/2017 | Faltys et al. | |
| 2017/0245379 A1 | 8/2017 | Kang | |
| 2017/0266448 A1 | 9/2017 | Tracey et al. | |
| 2017/0304613 A1 | 10/2017 | Faltys et al. | |
| 2017/0361093 A1 | 12/2017 | Yoo et al. | |
| 2018/0001096 A1 | 1/2018 | Faltys et al. | |
| 2018/0021217 A1 | 1/2018 | Tracey et al. | |
| 2018/0021580 A1 | 1/2018 | Tracey et al. | |
| 2018/0289970 A1 | 10/2018 | Faltys et al. | |
| 2019/0046799 A1 | 2/2019 | Levine et al. | |
| 2019/0111263 A1 | 4/2019 | Levine et al. | |
| 2019/0117979 A1 | 4/2019 | Tracey et al. | |
| 2020/0078589 A1 | 3/2020 | Simon et al. | |
| 2020/0330760 A1 | 10/2020 | Levine et al. | |
| 2020/0384259 A1 | 12/2020 | Chasensky et al. | |
| 2021/0315505 A1 | 10/2021 | Levine et al. | |
| 2021/0353949 A1 | 11/2021 | Faltys et al. | |
| 2022/0040483 A1 | 2/2022 | Levine et al. | |
| 2022/0118257 A1 | 4/2022 | Huston et al. | |
| 2022/0212001 A1 | 7/2022 | Faltys et al. | |
| 2022/0212012 A1 | 7/2022 | Manogue | |
| 2022/0362555 A1 | 11/2022 | Zitnik et al. | |
| 2023/0019961 A1 | 1/2023 | Huston et al. | |
| 2023/0117074 A1 | 4/2023 | Zanos et al. | |
| 2023/0144580 A1 | 5/2023 | Manogue | |
| 2023/0241387 A1 | 8/2023 | Levine et al. | |
| 2023/0321445 A1 | 10/2023 | Zanos et al. | |
| 2024/0215900 A1 | 7/2024 | Levine et al. | |

FOREIGN PATENT DOCUMENTS

| | | |
|---|---|---|
| CN | 101578067 A | 11/2009 |
| CN | 101868280 A | 10/2010 |
| CN | 104220129 A | 12/2014 |
| CN | 104602759 A | 5/2015 |
| DE | 2628045 A1 | 1/1977 |
| DE | 3736664 A1 | 5/1989 |
| DE | 20316509 U1 | 4/2004 |
| EP | 0438510 B1 | 8/1996 |
| EP | 0726791 B1 | 6/2000 |
| EP | 1001827 B1 | 1/2004 |
| EP | 2213330 A2 | 8/2010 |
| EP | 2073896 B1 | 10/2011 |
| GB | 04133 | 2/1910 |
| GB | 2073428 A | 10/1981 |
| JP | 2017502787 | 1/2017 |
| KR | 20050039445 A | 4/2005 |
| WO | WO93/01862 A1 | 2/1993 |
| WO | WO97/30998 A1 | 8/1997 |
| WO | WO98/20868 A1 | 5/1998 |
| WO | WO00/27381 A2 | 5/2000 |
| WO | WO00/47104 A2 | 8/2000 |
| WO | WO01/00273 A1 | 1/2001 |
| WO | WO01/08617 A1 | 2/2001 |
| WO | WO01/89526 A1 | 11/2001 |
| WO | WO02/44176 A1 | 6/2002 |
| WO | WO02/057275 A1 | 7/2002 |
| WO | WO03/072135 A2 | 9/2003 |
| WO | WO2004/000413 A2 | 12/2003 |
| WO | WO2004/064918 A1 | 8/2004 |
| WO | WO2006/073484 A1 | 7/2006 |
| WO | WO2006/076681 A2 | 7/2006 |
| WO | WO2007/133718 A2 | 11/2007 |
| WO | WO2010/005482 A1 | 1/2010 |
| WO | WO2010/067360 A2 | 6/2010 |
| WO | WO2010/118035 A2 | 10/2010 |

OTHER PUBLICATIONS

Manta et al.; Optimization of vagus nerve stimulation parameters using the firing activity of serotonin neurons in the rat dorsal raphe; European Neuropsychopharmacology; vol. 19; pp. 250-255; Jan. 2009 (doi: 10.1016/j.euroneuro.2008.12.001).

Pongratz et al.; The sympathetic nervous response in inflammation; Arthritis Research and Therapy; 16(504); 12 pages; retrieved from the internet (http://arthritis-research.com/content/16/6/504) ; Jan. 2014.

Abraham, Coagulation abnormalities in acute lung injury and sepsis, Am. J. Respir. Cell Mol. Biol., vol. 22(4), pp. 401-404, Apr. 2000.

Aekerlund et al., Anti-inflammatory effects of a new tumour necrosis factor-alpha (TNF-Alpha) inhibitor (CNI-1493) in collagen-

(56) References Cited

OTHER PUBLICATIONS induced arthritis (CIA) in rats, Clinical & Experimental Immunology, vol. 115, No. 1, pp. 32-41, Jan. 1, 1999.
Anderson et al.; Reflex principles of immunological homeostasis; Annu. Rev. Immunol.; 30; pp. 313-335; Apr. 2012.
Antonica, A., et al., Vagal control of lymphocyte release from rat thymus, J. Auton. Nerv. Syst., vol. 48(3), pp. 187-197, Aug. 1994.
Asakura et al., Non-surgical therapy for ulcerative colitis, Nippon Geka Gakkai Zasshi, vol. 98, No. 4, pp. 431-437, Apr. 1997 (abstract only).
Beliavskaia et al.," On the effects of prolonged stimulation of the peripheral segment of the vagus nerve . . .," Fiziologicheskii Zhurnal SSSR Imeni I.M. Sechenova., vol. 52(11); p. 1315-1321, Nov. 1966.
Ben-Noun et al.; Neck circumference as a simple screening measure for identifying overweight and obese patients; Obesity Research; vol. 9; No. 8; pp. 470-477; Aug. 8, 2001.
Benoist, et al., "Mast cells in autoimmune disease" Nature., vol. 420(19): pp. 875-878, Dec. 2002.
Benthem et al.; Parasympathetic inhibition of sympathetic neural activity to the pancreas; Am.J.Physiol Endocrinol.Metab; 280(2); pp. E378-E381; Feb. 2001.
Bernik et al., Vagus nerve stimulation attenuates cardiac TNF production in endotoxic shock, (supplemental to SHOCK, vol. 15, 2001, Injury, inflammation and sepsis: laboratory and clinical approaches, SHOCK, Abstracts, 24th Annual Conference on Shock, Marco Island, FL, Jun. 9-12, 2001), Abstract No. 81.
Bernik et al., Vagus nerve stimulation attenuates endotoxic shock and cardiac TNF production, 87th Clinical Congress of the American College of Surgeons, New Orleans, LA, Oct. 9, 2001.
Bernik et al., Vagus nerve stimulation attenuates LPS-induced cardiac TNF production and myocardial depression IN shock, New York Surgical Society, New York, NY, Apr. 11, 2001.
Bernik, et al., Pharmacological stimulation of the cholinergic anti-inflammatory pathway, The Journal of Experimental Medicine, vol. 195, No. 6, pp. 781-788, Mar. 18, 2002.
Besedovsky, H., et al., Immunoregulatory feedback between interleukin-1 and glucocorticoid hormones, Science, vol. 233, No. 4764, pp. 652-654, Aug. 1986.
Bhattacharya, S.K et al., Central muscarinic receptor subtypes and carrageenin-induced paw oedema in rats, Res. Esp. Med. Vol. 191(1), pp. 65-76, Dec. 1991.
Bianchi et al., Suppression of proinflammatory cytokines in monocytes by a tetravalent guanylhydrazone, Journal of Experimental Medicine, vol. 183, pp. 927-936, Mar. 1996.
Biggio et al.; Chronic vagus nerve stimulation induces neuronal plasticity in the rat hippocampus; Int. J. Neurpsychopharmacol.; vol. 12; No. 9; pp. 1209-1221; Oct. 2009.
Blackwell, T. S. et al., Sepsis and cytokines: current status, Br. J. Anaesth., vol. 77(1), pp. 110-117, Jul. 1996.
Blum, A. et al., Role of cytokines in heart failure, Am. Heart J., vol. 135(2), pp. 181-186, Feb. 1998.
Boldyreff, Gastric and intestinal mucus, its properties and physiological importance, Acta Medica Scandinavica (journal), vol. 89, Issue 1-2, pp. 1-14, Jan./Dec. 1936.
Borovikova et al., Acetylcholine inhibition of immune response to bacterial endotoxin in human macrophages, Abstracts, Society for Neuroscience, 29th Annual Meeting, Miami Beach, FL, (Abs. No. 624.6); Oct. 23-28, 1999.
Borovikova et al., Efferent vagus nerve activity attenuates cytokine-mediated inflammation, Society for Neuroscience Abstracts, vol. 26, No. 102, Nov. 4-9, 2000 (abstract only).
Borovikova et al., Intracerebroventricular CNI-1493 prevents LPS-induced hypotension and peak serum TNF at a four-log lower dose than systemic treatment, 21st Annual Conference on Shock, San Antonio, TX, Jun. 14-17, 1998, Abstract No. 86.
Borovikova et al., Role of the efferent vagus nerve signaling in the regulation of the innate immune response to LPS, (supplemental to SHOCK, vol. 13, 2000, Molecular, cellular, and systemic pathobiological aspects and therapeutic approaches, abstracts, 5th World Congress on Trauma, Shock inflammation and sepsis-pathophysiology, immune consequences and therapy, Feb. 29, 2000-Mar. 4, 2000, Munich, DE), Abstract No. 166.
Borovikova et al., Role of the vagus nerve in the anti-inflammatory effects of CNI-1493, the FASEB journal, vol. 14, no. 4, 2000 (Experimental Biology 2000, San Diego, CA, Apr. 15-18, 2000, Abstract No. 97.9).
Borovikova et al., Vagotomy blocks the protective effects of I.C.V. CNI-1493 against LPS-induced shock, (Supplemental to SHOCK, vol. 11, 1999, Molecular, cellular, and systemic pathobioloigal aspects and therapeutic approaches, abstacts and program, Fourth International Shock Congress and 22nd Annual Conference on Shock, Philadelphia, PA, Jun. 12-16, 1999), Abstract No. 277.
Borovikova, L. V., et al., Role of vagus nerve signaling in CNI-1493-mediated suppression of acute inflammation, Autonomic Neuroscience, vol. 85, No. 1-3, pp. 141-147, Dec. 20, 2000.
Borovikova, L. V., et al., Vagus nerve stimulation attenuates the systemic inflammatory response to endotoxin, Nature, vol. 405, No. 6785: pp. 458-462, May 25, 2000.
Bruchfeld et al.; Whole blood cytokine attenuation by cholinergic agonists ex vivo and relationship to vagus nerve activity in rheumatoid arthritis; J. Int. Med.; 268(1); pp. 94-101; Jul. 2010.
Bulloch et al.; Characterization of choline O-acetyltransferase (ChAT) in the BALB/C mouse spleen; Int.J.Neurosci.; 76(1-2); pp. 141-149; May 1994.
Bumgardner, G. L. et al., Transplantation and cytokines, Seminars in Liver Disease, vol. 19, No. 2, Thieme Medical Publishers; pp. 189-204, ©1999.
Burke et al., Bent pseudoknots and novel RNA inhibitors of type 1 human immunodeficiency virus (HIV-1) reverse transcriptase, J. Mol. Biol., vol. 264(4); pp. 650-666, Dec. 1996.
Bushby et al; Centiles for adult head circumference; Archives of Disease in Childhood; vol. 67(10); pp. 1286-1287; Oct. 1992.
Cano et al.; Characterization of the central nervous system innervation of the rat spleen using viral transneuronal tracing; J.Comp Neurol.; 439(1); pp. 1-18; Oct. 2001.
Carteron, N. L., Cytokines in rheumatoid arthritis: trials and tribulations, Mol. Med. Today, vol. 6(8), pp. 315-323, Aug. 2000.
Cavaillon et al.; The pro-inflammatory cytokine casade; Immune Response in the Critically Ill; Springer-Verlag Berlin Hiedelberg; pp. 37-66; Jan. 21, 2002.
Cheyuo et al.; The parasympathetic nervous system in the quest for stroke therapeutics; J. Cereb. Blood Flow Metab.; 31(5); pp. 1187-1195; May 2011.
Cicala et al., "Linkage between inflammation and coagulation: An update on the molecular basis of the crosstalk," Life Sciences, vol. 62(20); pp. 1817-1824, Apr. 1998.
Clark et al.; Enhanced recognition memory following vagus nerve stimulation in human subjects; Nat. Neurosci.; 2(1); pp. 94-98; Jan. 1999.
Cohen, "The immunopathogenesis of sepsis," Nature., vol. 420(6917): pp. 885-891, Dec. 2002.
Corcoran, et al., The effects of vagus nerve stimulation on pro- and anti-inflammatory cytokines in humans: a preliminary report, NeuroImmunoModulation, vol. 12(5), pp. 307-309, Sep. 2005.
Dake; Chronic cerebrospinal venous insufficiency and multiple sclerosis: Hostory and background; Techniques Vasc. Intervent. Radiol.; 15(2); pp. 94-100; Jun. 2012.
Das, Critical advances in spticemia and septic shock, Critical Care, vol. 4, pp. 290-296, Sep. 7, 2000.
Del Signore et al.; Nicotinic acetylcholine receptor subtypes in the rat sympathetic ganglion: pharmacological characterization, subcellular distribution and effect of pre-and postganglionic nerve crush; J.Neuropathol.Exp.Neurol.; 63(2); pp. 138-150; Feb. 2004.
Diamond et al.; Mapping the immunological homunculus; Proc. Natl. Acad. Sci. USA; 108(9); pp. 3461-3462; Mar. 1, 2011.
Dibbs, Z., et al., Cytokines in heart failure: pathogenetic mechanisms and potential treatment, Proc. Assoc. Am. Physicians, vol. 111, No. 5, pp. 423-428, Sep-Oct. 1999.
Dinarello, C. A., The interleukin-1 family: 10 years of discovery, FASEB J., vol. 8, No. 15, pp. 1314-1325, Dec. 1994.

(56) References Cited

OTHER PUBLICATIONS

Dorr et al.; Effect of vagus nerve stimulation on serotonergic and noradrenergic transmission; J. Pharmacol. Exp. Ther.; 318(2); pp. 890-898; Aug. 2006.

Doshi et al., Evolving role of tissue factor and its pathway inhibitor, Crit. Care Med., vol. 30, suppl. 5, pp. S241-S250, May 2002.

Elenkov et al.; Stress, corticotropin-releasing hormone, glucocorticoids, and the immune / inflammatory response: acute and chronic effects; Ann. N.Y. Acad. Sci.; 876; pp. 1-13; Jun. 22, 1999.

Ellington et al., In vitro selection of RNA molecules that bind specific ligands, Nature, vol. 346, pp. 818-822, Aug. 30, 1990.

Ellrich et al.; Transcutaneous vagus nerve stimulation; Eur. Neurological Rev.; 6(4); pp. 254-256; Winter 2011.

Engineer et al.; Directing neural plasticity to understand and treat tinnitus; Hear. Res.; 295; pp. 58-66; Jan. 2013.

Engineer et al.; Reversing pathological neural activity using targeted plasticity; Nature; 470(7332); pp. 101-104; Feb. 3, 2011 (Author Manuscript).

Esmon, The protein C pathway, Crit. Care Med., vol. 28, suppl. 9, pp. S44-S48, Sep. 2000.

Fields; New culprits in chronic pain; Scientific American; pp. 50-57; Nov. 2009.

Fleshner, M., et al., Thermogenic and corticosterone responses to intravenous cytokines (IL-1? and TNF-?) are attenuated by subdiaphragmatic vagotomy, J. Neuroimmunol., vol. 86(2), pp. 134-141, Jun. 1998.

Fox, D. A., Cytokine blockade as a new strategy to treat rheumatoid arthritis, Arch. Intern. Med., vol. 160, pp. 437-444, Feb. 28, 2000.

Fox, et al., Use of muscarinic agonists in the treatment of Sjorgren' syndrome, Clin. Immunol., vol. 101, No. 3; pp. 249-263, Dec. 2001.

Fujii et al.; Simvastatin regulates non-neuronal cholinergic activity in T lymphocytes via CD11a-mediated pathways; J. Neuroimmunol.; 179(1-2); pp. 101-107; Oct. 2006.

Gao et al.; Investigation of specificity of auricular acupuncture points in regulation of autonomic function in anesthetized rats; Autonomic Neurosc.; 138(1-2); pp. 50-56; Feb. 29, 2008.

Gattorno, M., et al., Tumor necrosis factor induced adhesion molecule serum concentrations in henoch-schoenlein purpura and pediatric systemic lupus erythematosus, J. Rheumatol., vol. 27, No. 9, pp. 2251-2255, Sep. 2000.

Gaykema, R. P., et al., Subdiaphragmatic vagotomy suppresses endotoxin-induced activation of hypothalamic corticotropin-releasing hormone neurons and ACTH secretion, Endocrinology, vol. 136, No. 10, pp. 4717-4720, Oct. 1995.

Ghelardini et al., S-(-)-ET 126: A potent and selective M1 antagonist in vitro and in vivo, Life Sciences, vol. 58, No. 12, pp. 991-1000, Feb. 1996.

Ghia, et al., The vagus nerve: a tonic inhibitory influence associated with inflammatory bowel disease in a murine model, Gastroenterology, vol. 131, No. 4, pp. 1122-1130, Oct. 2006.

Giebelen, et al., Stimulation of ?7 cholinergic receptors inhibits lipopolysaccharide-induced neutrophil recruitment by a tumor necrosis factor ?-independent mechanism, SHOCK, vol. 27, No. 4, pp. 443-447, Apr. 2007.

Goyal et al., Nature of the vagal inhibitory innervation to the lower esophageal sphincter, Journal of Clinical Investigation, vol. 55, pp. 1119-1126, May 1975.

Gracie, J. A., et al., A proinflammatory role for IL-18 in rheumatoid arthritis, J. Clin. Invest., vol. 104, No. 10, pp. 1393-1401, Nov. 1999.

Granert et al., Suppression of macrophage activation with CNI-1493 increases survival in infant rats with systemic haemophilus influenzae infection, Infection and Immunity, vol. 68, No. 9, pp. 5329-5334, Sep. 2000.

Green et al., Feedback technique for deep relaxation, Psycophysiology, vol. 6, No. 3, pp. 371-377, Nov. 1969.

Gregory et al., Neutrophil-kupffer-cell interaction in host defenses to systemic infections, Immunology Today, vol. 19, No. 11, pp. 507-510, Nov. 1998.

Groves et al.; Recordings from the rat locus coeruleus during acute vagal nerve stimulation in the anaesthetised rat; Neuroscience Letters; 379(3); pp. 174-179; May 13, 2005.

Guarente, Leonard, Ph. D.; Sirtuins, Aging, and Medicine; N Engl J Med ; vol. 364:pp. 2235-2244; Jun. 2011.

Guslandi, M., Nicotine treatment for ulcerative colitis, Br. J. Clin. Pharmacol., vol. 48(4), pp. 481-484, Oct. 1999.

Hansson, E.; Could chronic pain and spread of pain sensation be induced and maintained by glial activation ?. Acta Physiologica, vol. 187, Issue 1-2; pp. 321R327, May/Jun. 2006.

Harrison's Principles of Internal Medicine, 13th Ed., pp. 511-515 and 1433-1435, Mar. 1994.

Hatton et al.; Vagal nerve stimulation: overview and implications for anesthesiologists; Int'l Anesthesia Research Society; vol. 103; No. 5; pp. 1241-1249; Nov. 2006.

Hirano, T., Cytokine suppresive agent improves survival rate in rats with acute pancreatitis of closed duodenal loop, J. Surg. Res., vol. 81, No. 2, pp. 224-229, Feb. 1999.

Hirao et al., The limits of specificity: an experimental analysis with RNA aptamers to MS2 coat protein variants, Mol. Divers., vol. 4, No. 2, pp. 75-89, 1999 (Accepted Jan. 13, 1999).

Hoffer et al.; Implantable electrical and mechanical interfaces with nerve and muscle; Annals of Biomedical Engineering; vol. 8; pp. 351-360; Jul. 1980.

Holladay et al., Neuronal nicotinic acetylcholine receptors as targets for drug discovery, Journal of Medicinal Chemistry, 40(26), pp. 4169-4194, Dec. 1997.

Hommes, D. W. et al., Anti- and Pro-inflammatory cytokines in the pathogenesis of tissue damage in Crohn's disease, Current Opinion in Clinical Nutrition and Metabolic Care, vol. 3(3), pp. 191-195, May 2000.

Hsu, et al., Analysis of efficiency of magnetic stimulation, IEEE Trans. Biomed. Eng., vol. 50(11), pp. 1276-1285, Nov. 2003.

Hsu, H. Y., et al., Cytokine release of peripheral blood monoculear cells in children with chronic hepatitis B virus infection, J. Pediatr. Gastroenterol., vol. 29, No. 5, pp. 540-545, Nov. 1999.

Hu, et al., The effect of norepinephrine on endotoxin-mediated macrophage activation, J. Neuroimmunol., vol. 31(1), pp. 35-42, Jan. 1991.

Huston et al.; Splenectomy inactivates the cholinergic antiinflammatory pathway during lethal endotoxemia and polymicrobial sepsis; J. Exp. Med. 2006; vol. 203, No. 7; pp. 1623-1628; Jun. 19, 2006.

Huston et al.; Transcutaneous vagus nerve stimulation reduces serum high mobility group box 1 levels and improves survival in murine sepsis; Crit. Care Med.; 35(12); pp. 2762-2768; Dec. 2007.

Hutchinson et al.; Proinflammatory cytokines oppose opioid induced acute and chronic analgesia; Brain Behav Immun.; vol. 22; No. 8; pp. 1178-1189; Nov. 2008.

Ilton et al., "Differential expression of neutrophil adhesion molecules during coronary artery surgery with cardiopulmonary bypass" Journal of Thoracic and Cardiovascular Surgery, Mosby—Year Book, inc., St. Louis, MO, US, pp. 930-937, Nov. 1, 1999.

Jaeger et al., The structure of HIV-1 reverse transcriptase complexed with an RNA pseudoknot inhibitor, The EMBO Journal, 17(15), pp. 4535-4542, Aug. 1998.

Jander, S. et al., Interleukin-18 is induced in acute inflammatory demyelinating polymeuropathy, J. Neuroimmunol., vol. 114, pp. 253-258, Mar. 2001.

Joshi et al., Potent inhibition of human immunodeficiency virus type 1 replection by template analog reverse transcriptase , J. Virol., 76(13), pp. 6545-6557, Jul. 2002.

Kawahara et al.; SIRT6 links histone H3 lysine 9 deacetylation to NF-kappaB-dependent gene expression and organismal life span.; Cell. ; vol. 136; No. 1; pp. 62-74; Jan. 2009.

Kalishevskaya et al. "The character of vagotomy-and atropin-induced hypercoagulation," Sechenov Physiological Journal of the USSR, 65(3): pp. 398-404, Mar. 1979.

Kalishevskaya et al.; Nervous regulation of the fluid state of the blood; Usp. Fiziol. Nauk;, vol. 13; No. 2; pp. 93-122; Apr.-Jun. 1982.

(56) References Cited

OTHER PUBLICATIONS

Kanai, T. et al., Interleukin-18 and Crohn's disease, Digestion, vol. 63, suppl. 1, pp. 37-42, (year of pub. sufficiently earlier than effective US filing date and any foreign priority date) 2001.

Katagiri, M., et al., Increased cytokine production by gastric mucosa in patients with helicobacter pylori infection, J. Clin, Gastroenterol., vol. 25, Suppl. 1, pp. S211-S214, 1997.

Kawashima, et al., Extraneuronal cholinergic system in lymphocytes, Pharmacology & Therapeutics, vol. 86, pp. 29-48, Apr. 2000.

Kees et al.; Via beta-adrenoceptors, stimulation of extrasplenic sympathetic nerve fibers inhibits lipopolysaccharide-induced TNF secretion in perfused rat spleen; J.Neuroimmunol.; 145(1-2); pp. 77-85; Dec. 2003.

Kensch et al., HIV-1 reverse transcriptase-pseudoknot RNA aptamer interaction has a binding affinity in the low picomolar range coupled with high specificity, J. Biol. Chem., 275(24), pp. 18271-18278, Jun. 16, 2000.

Khatun, S., et al., "Induction of hypercoagulability condition by chronic localized cold stress in rabbits," Thromb. and Haemost., 81(3): pp. 449-455, Mar. 1999.

Kimball, et al., Levamisole causes differential cytokine expression by elicited mouse peritoneal macrophases, Journal of Leukocyte Biology, vo. 52, No. 3, pp. 349-356, Sep. 1992 (abstract only).

Kimmings, A. N., et al., Systemic inflammatory response in acute cholangitis and after subsequent treatment, Eur. J. Surg., vol. 166, pp. 700-705, Sep. 2000.

Kirchner et al.; Left vagus nerve stimulation suppresses experimentally induced pain; Neurology; vol. 55; pp. 1167-1171; Oct. 2000.

Kokkula, R. et al., Successful treatment of collagen-induced arthritis in mice and rats by targeting extracellular high mobility group box chromosomal protein 1 activity, Arthritis Rheum., 48(7), pp. 2052-2058, Jul. 2003.

Koopman et al.; Pilot study of stimulation of the cholinergic anti-inflammatory pathway with an implantable vagus nerve stimulation device in patients with rheumatoid arthritis; Arth. Rheum.; 64(10 suppl.); pp. S195; Oct. 2012.

Krarup et al; Conduction studies in peripheral cat nerve using implanted electrodes: I. methods and findings in controls; Muscle & Nerve; vol. 11; pp. 922-932; Sep. 1988.

Kudrjashov, et al. "Reflex nature of the physiological anticoagulating system," Nature, vol. 196(4855): pp. 647-649; Nov. 17, 1962.

Kumins, N. H., et al., Partial hepatectomy reduces the endotoxin-induced peak circulating level of tumor necrosis factor in rats, SHOCK, vol. 5, No. 5, pp. 385-388, May 1996.

Kuznik, "Role of the vascular wall in the process of hemostatis," Usp Sovrem Biol., vol. 75(1): pp. 61-85, 1973.

Kuznik, et al., "Blood Coagulation in stimulation of the vagus nerve in cats," Biull. Eskp. Biol. Med., vol. 78(7): pp. 7-9, 1974.

Kuznik, et al., "Heart as an efferent regulator of the process of blood coagulation and fibrinolysis," Kardiologiia, vol. 13(3): pp. 10-17, 1973.

Kuznik, et al., "Role of the heart and vessels in regulating blood coagulation and fibrinolysis," Kagdiologiia, vol. 13(4): pp. 145-154, 1973.

Kuznik, et al., "Secretion of blood coagulation factors into saliva under conditions of hypo-and hypercoagulation," Voprosy Meditsinskoi Khimii, vol. 19(1): pp. 54-57; 1973.

Kuznik, et al., "The dynamics of procoagulatible and fibrinolytic activities during electrical stimulation of peripheral nerves," Sechenov Physiological Journal of the USSR, vol. 65; No. 3: pp. 414-420, Mar. 1979.

Kuznik, et al., "The role of the vascular wall in the mechanism of control of blood coagulation and fibrinolysis on stimulation of the vagus nerve," Cor Vasa, vol. 17(2): pp. 151-158, 1975.

Lang, et al., "Neurogienic control of cerebral blood flow," Experimental Neurology, 43(1): pp. 143-161, Apr. 1974.

Lee, H. G., et al., Peritoneal lavage fluids stimulate NIH3T3 fibroblast proliferation and contain increased tumour necrosis factor and IL6 in experimental silica-induced rat peritonitis, Clin. Exp. Immunol., vol. 100, pp. 139-144, Apr. 1995.

LeNovere, N. et al., Molecular evolution of the nicotinic acetylcholine receptor: an example of multigene family in excitable cells, J. Mol. Evol., 40, pp. 155-172, Feb. 1995.

Leonard, S. et al., Neuronal nicotinic receptors: from structure to function, Nicotine & Tobacco Res. 3:203-223, Aug. 2001.

Lips et al.; Coexpression and spatial association of nicotinic acetylcholine receptor subunits alpha7 and alpha10 in rat sympathetic neurons; J.Mol.Neurosci.; 30; pp. 15-16; Feb. 2006.

Lipton, J. M. et al.; Anti-inflammatory actions of the neuroimmunomodulator ?-MSH, Immunol. Today, vol. 18, pp. 140-145, Mar. 1997.

Loeb et al.; Cuff electrodes for chronic stimulation and recording of peripheral nerve activity; Journal of Neuroscience Methods; vol. 64; pp. 95-103; Jan. 1996.

Madretsma, G. S., et al., Nicotine inhibits the in vitro production of interleukin 2 and tumour necrosis factor-alpha by human monocuclear cells, Immunopharmacology, vol. 35, No. 1, pp. 47-51, Oct. 1996.

Martindale: The Extra Pharmacopoeia; 28th Ed. London; The Pharmaceutical Press; pp. 446-485; ©1982.

Martiney et al., Prevention and treatment of experimental autoimmune encephalomyelitis by CNI-1493, a macrophage-deactivating agent, Journal of Immunology, vol. 160, No. 11, pp. 5588-5595, Jun. 1, 1998.

McGuinness, P. H., et al., Increases in intrahepatic CD68 positive cells, MAC387 positive cells, and proinflammatory cytokines (particulary interleukin 18) in chronic hepatitis C infection, Gut, vol. 46(2), pp. 260-269, Feb. 2000.

Miguel-Hidalgo, J.J.; The role of glial cells in drug abuse; Current Drug Abuse Reviews; vol. 2; No. 1; pp. 76-82; Jan. 2009.

Milligan et al.; Pathological and protective roles of glia in chronic pain; Nat Rev Neurosci.; vol. 10; No. 1; pp. 23-26; Jan. 2009.

Minnich et al.; Anti-cytokine and anti-inflammatory therapies for the treatment of severe sepsis: progress and pitfalls; Proceedings of the Nutrition Society; vol. 63(3); pp. 437-441; Aug. 2004.

Mishchenko, et al., "Coagulation of the blood and fibrinolysos in dogs during vagal stimulation," Sechenov Physiological Journal of the USSR, vol. 61(1): pp. 101-107, 1975.

Mishchenko, "The role of specific adreno-and choline-receptors of the vascular wall in the regulation of blood coagulation in the stimulation of the vagus nerve," Biull. Eskp. Biol. Med., vol. 78(8): pp. 19-22, 1974.

Molina et al., CNI-1493 attenuates hemodynamic and pro-inflammatory responses to LPS, Shock, vol. 10, No. 5, pp. 329-334, Nov. 1998.

Nadol et al., "Surgery of the Ear and Temporal Bone," Lippinkott Williams & Wilkins, 2nd Ed., 2005, (Publication date: Sep. 21, 2004), p. 580.

Nagashima et al., Thrombin-activatable fibrinolysis inhibitor (TAFI) deficiency is compatible with murine life, J. Clin. Invest., 109, pp. 101-110, Jan. 2002.

Nathan, C. F., Secretory products of macrophages, J. Clin. Invest., vol. 79 (2), pp. 319-326, Feb. 1987.

Navalkar et al.; Irbesartan, an angiotensin type 1 receptor inhibitor, regulates markers of inflammation in patients with premature atherosclerosis; Journal of the American College of Cardiology; vol. 37; No. 2; pp. 440-444; Feb. 2001.

Navzer et al.; Reversing pathological neural activity using targeted plasticity; Nature; 470(7332); pp. 101-104; Feb. 3, 2011.

Neuhaus et al.; P300 is enhanced in responders to vagus nerve stimulation for treatment of major depressive disorder; J. Affect. Disord.; 100(1-3); pp. 123-128; Jun. 2007.

Noguchi et al., Increases in Gastric acidity in response to electroacupuncture stimulation of hindlimb of anesthetized rats, Jpn. J. Physiol., 46(1), pp. 53-58, Feb. 1996.

Norton, Can ultrasound be used to stimulate nerve tissue, BioMedical Engineering OnLine, 2(1), pp. 6, Mar. 4, 2003.

Olofsson et al.; Rethinking inflammation: neural circuits in the regulation of immunity; Immunological Reviews; 248(1); pp. 188-204; Jul. 2012.

Oshinsky et al.; Non-invasive vagus nerve stimulation as treatment for trigeminal allodynia; Pain; 155(5); pp. 1037-1042; May 2014.

Palmblad et al., Dynamics of early synovial cytokine expression in rodent collagen-induced arthritis: a thereapeutic study unding a

(56) References Cited

OTHER PUBLICATIONS macrophage-deactivation compound, American Journal of Pathology, vol. 158, No. 2, pp. 491-500, Feb. 2, 2001.

Pateyuk, et al., "Treatment of Botkin's disease with heparin," Klin. Med., vol. 51(3): pp. 113-117, Mar. 1973.

Pavlov et al.; Controlling inflammation: the cholinergic anti-inflammatory pathway; Biochem. Soc. Trans.; 34(Pt 6); pp. 1037-1040; Dec. 2006.

Payne, J. B. et al., Nicotine effects on PGE2 and IL-1 beta release by LPS-treated human monocytes, J. Perio. Res., vol. 31, No. 2, pp. 99-104, Feb. 1996.

Peuker; The nerve supply of the human auricle; Clin. Anat.; 15(1); pp. 35-37; Jan. 2002.

Prystowsky, J. B. et al., Interleukin-1 mediates guinea pig gallbladder inflammation in vivo, J. Surg. Res., vol. 71, No. 2, pp. 123-126, Aug. 1997.

Pulkki, K. J., Cytokines and cardiomyocyte death, Ann. Med., vol. 29(4), pp. 339-343, Aug. 1997.

Pullan, R. D., et al., Transdermal nicotine for active ulceratiive colitis, N. Engl. J. Med., vol. 330, No. 12, pp. 811-815, Mar. 24, 1994.

Pulvirenti et al; Drug dependence as a disorder of neural plasticity:focus on dopamine and glutamate; Rev Neurosci.; vol. 12; No. 2; pp. 141-158; Apr./Jun. 2001.

Rahman et al.; Mammalian Sirt 1: Insights on its biological functions; Cell Communications and Signaling; vol. 9; No. 11; pp. 1-8; May 2011.

Rayner, S. A. et al., Local bioactive tumour necrosis factor (TNF) in corneal allotransplantation, Clin. Exp. Immunol., vol. 122, pp. 109-116, Oct. 2000.

Reale et al.; Treatment with an acetylcholinesterase inhibitor in alzheimer patients modulates the expression and production of the pro-inflammatory and anti-inflammatory cytokines; J. Neuroimmunology; 148(1-2); pp. 162-171; Mar. 2004.

Rinner et al.; Rat lymphocytes produce and secrete acetylcholine in dependence of differentiation and activation; J.Neuroimmunol.; 81(1-2); pp. 31-37; Jan. 1998.

Robinson et al.; Studies with the Electrocardiogram the Action of the Vagus Nerve on the Human Heart; J Exp Med; 14(3):217-234; Sep. 1911.

Romanovsky, A. A., et al., The vagus nerve in the thermoregulatory response to systemic inflammation, Am. J. Physiol., vol. 273, No. 1 (part 2), pp. R407-R413, Jul. 1, 1997.

Saghizadeh et al.; The expression of TNF? by human muscle; J. Clin. Invest.; vol. 97; No. 4; pp. 1111-1116; Feb. 15, 1996.

Saindon et al.; Effect of cervical vagotomy on sympathetic nerve responses to peripheral interleukin-1beta; Auton.Neuroscience Basic and Clinical; 87; pp. 243-248; Mar. 23, 2001.

Saito, Involvement of muscarinic M1 receptor in the central pathway of the serotonin-induced bezold-jarisch reflex in rats, J. Autonomic Nervous System, vol. 49, pp. 61-68, Sep. 1994.

Sandborn, W. J., et al., Transdermal nicotine for mildly to moderately active ulcerative colitis, Ann. Intern. Med, vol. 126, No. 5, pp. 364-371, Mar. 1, 1997.

Sato, E., et al., Acetylcholine stimulates alveolar macrophages to release inflammatory cell chemotactic activity, Am. J. Physiol., vol. 274, pp. L970-L979, Jun. 1998.

Sato, K.Z., et al., Diversity of mRNA expression for muscarinic acetylcholine receptor subtypes and neuronal nicotinic acetylcholine receptor subunits in human mononuclear leukosytes and leukemic cell lines, Neuroscience Letters, vol. 266, pp. 17-20, Apr. 30, 1999.

Scheinman, R. I., et al., Role of transcriptional activation of I?B? in mediation of immunosuppression by glucocorticoids, Science, vol. 270, No. 5234, pp. 283-286, Oct. 13, 1995.

Schneider et al., High-affinity ssDNA inhibitors of the review transcriptase of type 1 human immunodeficiency virus, Biochemistry, 34(29), pp. 9599-9610, Jul. 1995.

Shafer, Genotypic testing for human immunodeficiency virus type 1 drug resistance, Clinical Microbiology Reviews, vol. 15, pp. 247-277, Apr. 2002.

Shapiro et al.; Prospective, randomised trial of two doses of rFVIIa (NovoSeven) in haemophilia patients with inhibitors undergoing surgery; Thromb Haemost; vol. 80(5); pp. 773-778; Nov. 1998.

Sher, M. E., et al., The influence of cigarette smoking on cytokine levels in patients with inflammatory bowel disease, Inflamm. Bowel Dis., vol. 5, No. 2, pp. 73-78, May 1999.

Shi et al.; Effects of efferent vagus nerve excitation on inflammatory response in heart tissue in rats with endotoxemia; vol. 15, No. 1; pp. 26-28; Jan. 2003 (Eng. Abstract).

Snyder et al., Correction of hemophilia B in canine and murine models using recombinant adeno-associated viral vectors; Nature Medicine, 5(1), pp. 64-70, Jan. 1999.

Sokratov, et al. "The role of choline and adrenegic structures in regulation of renal excretion of hemocoagulating compounds into the urine," Sechenov Physiological Journal of the USSR, vol. 63(12): pp. 1728-1732, 1977.

Stalcup et al., Endothelial cell functions in the hemodynamic responses to stress, Annals of the New York Academy of Sciences, vol. 401, pp. 117-131, Dec. 1982.

Steinlein, New functions for nicotine acetylcholine receptors?, Behavioural Brain Res., vol. 95(1), pp. 31-35, Sep. 1998.

Sternberg, E. M., Perspectives series: cytokines and the brain 'neural-immune interactions in health and disease,' J. Clin. Invest., vol. 100, No. 22, pp. 2641-2647, Dec. 1997.

Stevens et al.; The anti-inflammatory effect of some immunosuppressive agents; J. Path.; 97(2); pp. 367-373; Feb. 1969.

Strojnik et al.; Treatment of drop foot using and implantable peroneal underknee stimulator; Scand. J. Rehab. Med.; vol. 19(1); pp. 37R43; Dec. 1986.

Sugano et al., Nicotine inhibits the production of inflammatory mediators in U937 cells through modulation of nuclear factor-kappaβ activation, Biochemical and Biophysical Research Communications, vol. 252, No. 1, pp. 25-28, Nov. 9, 1998.

Suter et al.; Do glial cells control pain ?; Neuron Glia Biol.; vol. 3; No. 3; pp. 255-268; Aug. 2007.

Swick et al.; Locus coeruleus neuronal activity in awake monkeys: relationship to auditory P300-like potentials and spontaneous EEG. Exp. Brain Res.; 101(1); pp. 86-92; Sep. 1994.

Sykes, et al., An investigation into the effect and mechanisms of action of nicotine in inflammatory bowel disease, Inflamm. Res., vol. 49, pp. 311-319, Jul. 2000.

Takeuchi et al., A comparison between chinese blended medicine "Shoseiryuto" tranilast and ketotifen on the anit-allergic action in the guinea pigs, Allergy, vol. 34, No. 6, pp. 387-393, Jun. 1985 (eng. abstract).

Tekdemir et al.; A clinico-anatomic study of the auricular branch of the vagus nerve and arnold's ear-cough reflex; Surg. Radiol. Anat.; 20(4); pp. 253-257; Mar. 1998.

Toyabe, et al., Identification of nicotinic acetylcholine receptors on lymphocytes in the periphery as well as thymus in mice, Immunology, vol. 92(2), pp. 201-205, Oct. 1997.

Tracey et al., Mind over immunity, FASEB Journal, vol. 15, No. 9, pp. 1575-1576, Jul. 2001.

Tracey, K. J. et al., Anti-cachectin/TNF monoclonal antibodies prevent septic shock during lethal bacteraemia; Nature, 330: pp. 662-664, Dec. 23, 1987.

Tracey, K. J. et al., Physiology and immunology of the cholinergic antiinflammatory pathway; J Clin Invest.; vol. 117: No. 2; pp. 289-296; Feb. 2007.

Tracey, K. J.; Reflex control of immunity; Nat Rev Immunol; 9(6); pp. 418-428; Jun. 2009.

Tracey, K. J. et al., Shock and tissue injury induced by recombinant human cachectin, Science, vol. 234, pp. 470-474, Oct. 24, 1986.

Tracey, K.J., The inflammatory reflex, Nature, vol. 420, pp. 853-859, Dec. 19-26, 2002.

Tsutsui, H., et al., Pathophysiolocical roles of interleukin-18 in inflammatory liver diseases; Immunol. Rev., 174:192-209, Apr. 2000.

(56) References Cited

OTHER PUBLICATIONS

Tuerk et al., RNA pseudoknots that inhibit human immunodeficiency virus type 1 reverse transcriptase; Proc. Natl. Acad. Sci. USA, 89, pp. 6988-6992, Aug. 1992.

Tuerk et al., Systematic evolution of ligands by exponential enrichment: RNA ligands to bacteriophage T4 DNA polymerase; Science, 249(4968), pp. 505-510, Aug. 3, 1990.

Van Dijk, A. P., et al., Transdermal nictotine inhibits interleukin 2 synthesis by mononuclear cells derived from healthy volunteers, Eur. J. Clin. Invest, vol. 28, pp. 664-671, Aug. 1998.

Van Der Horst et al.; Stressing the role of FoxO proteins in lifespan and disease; Nat Rev Mol Cell Biol.; vol. 8; No. 6; pp. 440-450; Jun. 2007.

Vanhoutte, et al., Muscarinic and beta-adrenergic prejunctional modulation of adrenergic neurotransmission in the blood vessel wall, Gen Pharmac., vol. 14(1), pp. 35-37, Jan. 1983.

vanWesterloo, et al., The cholinergic anti-inflammatory pathway regulates the host response during septic peritonitis, The Journal of Infectious Diseases, vol. 191, pp. 2138-2148, Jun. 15, 2005.

Ventureyra, Transcutaneous vagus nerve stimulation for partial onset seizure therapy, Child's Nerv Syst, vol. 16(2), pp. 101-102, Feb. 2000.

Vijayaraghavan, S.; Glial-neuronal interactions-implications for plasticity anddrug addictionl Aaps J.; vol. 11; No. 1; pp. 123-132; Mar. 2009.

Villa et al., Protection against lethal polymicrobial sepsis by CNI-1493, an inhibitor of pro-inflammatory cytokine synthesis, Journal of Endotoxin Research, vol. 4, No. 3, pp. 197-204, Jun. 1997.

Von Känel, et al., Effects of non-specific ?-adrenergic stimulation and blockade on blood coagulation in hypertension, J. Appl. Physiol., vol. 94, pp. 1455-1459, Apr. 2003.

Von Känel, et al., Effects of sympathetic activation by adrenergic infusions on hemostasis in vivo, Eur. J. Haematol., vol. 65: pp. 357-369, Dec. 2000.

Walland et al., Compensation of muscarinic brochial effects of talsaclidine by concomitant sympathetic activation in guinea pigs; European Journal of Pharmacology, vol. 330(2-3), pp. 213-219, Jul. 9, 1997.

Wang et al; Nicotinic acetylcholine receptor alpha7 subunit is an essential regulator of inflammation; Nature; 421; 384-388; Jan. 23, 2003.

Wang, H., et al., HMG-1 as a late mediator of endotoxin lethality in mice, Science, vol. 285, pp. 248-251, Jul. 9, 1999.

Waserman, S. et al., TNF-? dysregulation in asthma: relationship to ongoing corticosteroid therapy, Can. Respir. J., vol. 7, No. 3, pp. 229-237, May-Jun. 2000.

Watanabe, H. et al., The significance of tumor necrosis factor (TNF) levels for rejection of joint allograft, J. Reconstr. Microsurg., vol. 13, No. 3, pp. 193-197, Apr. 1997.

Wathey, J.C. et al., Numerical reconstruction of the quantal event at nicotinic synapses; Biophys. J., vol. 27: pp. 145-164, Jul. 1979.

Watkins, L.R. et al., Blockade of interleukin-1 induced hyperthermia by subdiaphragmatic vagotomy: evidence for vagal mediation of immune-brain communication, Neurosci. Lett., vol. 183(1-2), pp. 27-31, Jan. 1995.

Watkins, L.R. et al., Implications of immune-to-brain communication for sickness and pain, Proc. Natl. Acad. Sci. U.S.A., vol. 96(14), pp. 7710-7713, Jul. 6, 1999.

Webster's Dictionary, definition of "intrathecal", online version accessed Apr. 21, 2009.

Weiner, et al., "Inflammation and therapeutic vaccination in CNS diseases," Nature., vol. 420(6917): pp. 879-884, Dec. 19-26, 2002.

Westerheide et al.; Stress-inducible regulation of heat shock factor 1 by the deacetylase SIRT1.; Science; Vo. 323; No. 5717; pp. 1063-1066; Feb. 2009.

Whaley, K. et al., C2 synthesis by human monocytes is modulated by a nicotinic cholinergic receptor, Nature, vol. 293, pp. 580-582, Oct. 15, 1981.

Woiciechowsky, C. et al., Sympathetic activation triggers systemic interleukin-10 release in immunodepression induced by brain injury, Nature Med., vol. 4, No. 7, pp. 808-813, Jul. 1998.

Yeh, S.S. et al., Geriatric cachexia: the role of cytokines, Am. J. Clin. Nutr., vol. 70(2), pp. 183-197, Aug. 1999.

Yu et al.; Low-level transcutaneous electrical stimulation of the auricular branch of the vagus nerve: a non-invasive approach to treat the initial phase of atrial fibrillation; Heart Rhythm; 10(3); pp. 428-435; Mar. 2013.

Zamotrinsky et al.; Vagal neurostimulation in patients with coronary artery disease; Auton. Neurosci.; 88(1-2); pp. 109-116; Apr. 2001.

Zhang et al., Tumor necrosis factor, The Cytokine Handbook, 3rd ed., Ed. Thompson, Academic Press, pp. 517-548, Jul. 1, 1998.

Zhang et al.; Roles of SIRT1 in the acute and restorative phases following induction of inflammation.; J Biol Chem.; vol. 285; No. 53; pp. 41391-401; Dec. 2010.

Zhang et al.; Chronic vagus nerve stimulation improves autonomic control and attenuates systemic inflammation and heart failure progression in a canine high-rate pacing model; Circulation Heart Fail.; 2; pp. 692-699; Nov. 2009.

Zhao et al.; Transcutaneous auricular vagus stimulation protects endotoxemic rat from lipopolysaccharide-induced inflammation; Evid. Based Complement Alternat. Med.; vol. 2012; Article ID 627023; 10 pages; Dec. 29, 2012.

Faltys et al.; U.S. Appl. No. 16/292,144 entitled "Nerve cuff with pocket for leadless stimulator," filed Mar. 4, 2019.

Zitnik et al.; U.S. Appl. No. 16/356,906 entitled "Batteryless Implantable Microstimulators," filed Mar. 18, 2019.

Strowig et al.; Inflammasomes in health and disease; Nature; vol. 481; pp. 278-286; doi: 10.1038/nature10759; Jan. 19, 2012.

Faltys et al.; U.S. Appl. No. 16/544,805 entitled "Nerve cuff with pocket for leadless stimulator," filed Aug. 19, 2019.

Faltys et al.; U.S. Appl. No. 16/544,882 entitled "Neural stimulation devices and systems for treatment of chronic inflammation," filed Aug. 19, 2019.

Manogue; U.S. Appl. No. 16/582,726 entitled "Methods and apparatuses for reducing bleeding via coordinated trigeminal and vagal nerve stimulation," filed Sep. 25, 2019.

Faltys et al.; U.S. Appl. No. 16/728,880 entitled "Implantable neurostimulator having power control and thermal regulation and methods of use," filed Dec. 27, 2019.

Faltys et al.; U.S. Appl. No. 16/785,400 entitled "Systems and methods for establishing a nerve block," filed Feb. 7, 2020.

Koopman et al.; Pilot study of stimulation of the cholinergic anti-inflammatory pathway with an implantable vagus nerve stimulation device in patients with rheumatoid arthritis; 2012 ACR/ARHP Annual Meeting; Abstract No. 451; 4 pages; retrieved from the internet (https://acrabstracts.org/abstract/pilot-study-of-stimulation-of-the-cholinergic-anti-inflammatory-pathway-with-an-implantable-vagus-nerve-stimulation-device-in-patients-with-rheumatoid-arthritis); (Abstract Only); on Sep. 24, 2020.

Pavlov et al.; The cholinergic anti-inflammatory pathway; Brain, Behavior, and Immunity; 19; p. 493-499; Nov. 2005.

Zitnik et al.; Treatment of chronic inflammatory diseases with implantable medical devices; Cleveland Clinic Journal of Medicine; 78(Suppl 1); pp. S30-S34; Aug. 2011.

Katsavos et al.; Biomarkers in multiple sclerosis: an up-to-date overview; Multiple Sclerosis International; vol. 2013, Article ID 340508, 20 pages; (year of pub. sufficiently earlier than effective US filing date and any foreign priority date) 2013.

Palov et al.; The cholinergic anti-inflammatory pathway: a missing link in neuroimmunomodulation; Molecular Medicine; 9(5); pp. 125-134; May 2003.

Tracey et al.; U.S. Appl. No. 17/170,772 entitled "Treatment of bleeding by non-invasive stimulation," filed Feb. 8, 2021.

Levine et al.; U.S. Appl. No. 17/599,594 entitled "Vagus nerve stimulation to treat neurodegenerative disorders," filed Sep. 29, 2021.

Koopman et al.; THU0237 first-in-human study of vagus nerve stimulation for rheumatoid arthritis: clinical and biomarker results through day 84; Annals of the Rheumatic Diseases; 72(Suppl 3):A245; Jun. 1, 2013 (Abstract Only).

(56) References Cited

OTHER PUBLICATIONS

Mayo Clinic; The factsheet of vagus nerve stimulation from the Mayo Clinic website: www.mayoclinic.org/tests-procedures/vagus-nerve-sti mulation/about/pac-20384565; retrieved from the internet on Sep. 28, 2021.

Levine et al.; U.S. Appl. No. 17/728,765 entitled "Systems and methods for stimulating and/or monitoring loci in the brain to treat inflammation and to enhance vagus nerve stimulation," filed Apr. 25, 2022.

Faltys et al.; U.S. Appl. No. 17/751,505 entitled "Implantable neurostimulator having power control and thermal regulation and methods of use," filed May 23, 2022.

De Jonge et al.; Stimulation of the vagus nerve attenuates macrophage activation by activating the Jak2-STAT3 signaling pathway; Nature Immunology; 6(8); pp. 844-851; Aug. 2005.

Rendas-Baum et al.; Evaluating the efficacy of sequential biologic therapies for rheumatoid arthritis patients with an inadequate response to tumor necrosis factor-alpha inhibitors; Arthritis research and therapy; 13; R25; 15 pages; ; Feb. 2011.

Rosas-Ballina et al.; Acetylcholine-synthesizing T cells relay neural signals in a vagus nerve circuit Science; 334(6052); pp. 98-101; 10 pages; (Author Manuscript); Oct. 2011.

Vida et al.; Aplha 7-cholinergic receptor mediates vagal induction of splenic norepinephrine; Journal of Immunology; 186(7); pp. 4340-4346; 16 pages; (Author Manuscript); Apr. 2011.

Levine et al.; U.S. Appl. No. 18/151,407 entitled "Control of vagal stimulation," filed Jan. 6, 2023.

Huston et al.; U.S. Appl. No. 18/355,401 entitled "Methods for reducing bleeding in hemophilia by vagus nerve stimualtion to prime platelets," filed Jul. 19, 2023.

Yang et al.; Axon myelination and electrical stimulation in a microfluidic, compartmentalized cell culture platform; Neuromolecular medicine; vol. 14; pp. 112-118; Jun. 2012.

Calle et al.; U.S. Appl. No. 18/562,283 entitled "Neurostimulation parameter authentication and expiration system for nuerostimulation," filed Nov. 17, 2023.

Levine et al.; U.S. Appl. No. 18/431,974 entitled "Vagus nerve stimulation pre-screening test," filed Feb. 3, 2024.

Zitnik et al.; U.S. Appl. No. 18/604,465 entitled "Batteryless implantable microsimulators, " filed Mar. 13, 2024.

Levine; U.S. Appl. No. 18/605,809 entitled "Bimodal vagus nerve simulation to treat neurodegenerative disorders, " filed Mar. 14, 2024.

Gautron et al.; Neurobiology of inflammation-associated anorexia; Frontiers in Neuroscience; 3(59); 10 pages; Jan. 8, 2010.

Li et al.; U.S. Appl. No.18/645,129 entitled "System and methods of stimulation at trigeminaly innervated regions for disorders of cerebral perfusion," filed Apr. 24, 2024.

Levine et al.; U.S. Appl. No. 18/664,817 entitled "Reversing demyelination," filed May 15, 2024.

Levine et al.; U.S. Appl. No. 18/730,753 entitled "Treatment of inflammatory disorders," filed Jul. 19, 2024.

Hebb et al.; Creating the Feedback Loop: Closed-Loop Neurostimulation; Neurosurgery Clinics of North America; 25(1); pp. 187-204; Jan. 28, 2014.

Levine et al.; U.S. Appl. No. 18/893,907 entitled "Control of vagal stimulation," filed Sep. 23, 2024.

* cited by examiner

EXTREMELY LOW DUTY-CYCLE ACTIVATION OF THE CHOLINERGIC ANTI-INFLAMMATORY PATHWAY TO TREAT CHRONIC INFLAMMATION

CROSS REFERENCE TO RELATED APPLICATIONS

This application is a continuation of U.S. patent application Ser. No. 14/968,702, filed Dec. 14, 2015, titled "EXTREMELY LOW DUTY-CYCLE ACTIVATION OF THE CHOLINERGIC ANTI-INFLAMMATORY PATHWAY TO TREAT CHRONIC INFLAMMATION," now U.S. Pat. No. 9,849,286, which is a continuation of U.S. patent application Ser. No. 14/336,942, filed Jul. 21, 2014, titled "EXTREMELY LOW DUTY-CYCLE ACTIVATION OF THE CHOLINERGIC ANTI-INFLAMMATORY PATHWAY TO TREAT CHRONIC INFLAMMATION," now U.S. Pat. No. 9,211,410, which is a continuation-in-part of U.S. patent application Ser. No. 13/467,928, filed May 9, 2012, titled "SINGLE-PULSE ACTIVATION OF THE CHOLINERGIC ANTI-INFLAMMATORY PATHWAY TO TREAT CHRONIC INFLAMMATION," now U.S. Pat. No. 8,788,034, which claims the benefit of U.S. Provisional Patent Application No. 61/484,112, filed May 9, 2011, and titled "SINGLE-PULSE ACTIVATION OF THE CHOLINERGIC ANTI-INFLAMMATORY PATHWAY TO TREAT CHRONIC INFLAMMATION," each of which is hereby incorporated by reference in its entirety.

This patent application may be related to any of the following patent and pending patent applications: U.S. patent application Ser. No. 12/434,462, filed May 1, 2009, titled "VAGUS NERVE STIMULATION ELECTRODES AND METHODS OF USE," Publication No. US-2009-0275997-A1; U.S. patent application Ser. No. 12/620,413, filed Nov. 17, 2009, entitled "DEVICES AND METHODS FOR OPTIMIZING ELECTRODE PLACEMENT FOR ANTI-INFLAMMATORY STIMULATION," now U.S. Pat. No. 8,412,338; U.S. patent application Ser. No. 12/874,171, filed Sep. 1, 2010, titled "PRESCRIPTION PAD FOR TREATMENT OF INFLAMMATORY DISORDERS," Publication No. US-2011-0054569-A1; U.S. patent application Ser. No. 12/917,197, filed Nov. 1, 2010, titled "MODULATION OF THE CHOLINERGIC ANTI-INFLAMMATORY PATHWAY TO TREAT PAIN OR ADDICTION," Publication No. US-2011-0106208-A1; U.S. patent application Ser. No. 12/978,250, filed Dec. 23, 2010, titled "NEURAL STIMULATION DEVICES AND SYSTEMS FOR TREATMENT OF CHRONIC INFLAMMATION," now U.S. Pat. No. 8,612,002; and U.S. patent application Ser. No. 12/797,452, filed Jun. 9, 2010 and entitled "NERVE CUFF WITH POCKET FOR LEADLESS STIMULATOR," Publication No. US-2010-0312320-A1.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present invention relates generally to systems and devices for treatment of disorders, including chronic inflammation and inflammatory disorders using extremely low duty-cycle stimulation. In particular, described herein are systems, devices and methods for treating disorders such as intestinal inflammatory disorders. Further described herein generally are methods and devices, including an implantable microstimulators, adapted for electrically stimulating the vagus nerve to treat chronic inflammation by extremely low duty cycle stimulation to modulate an inflammatory response (via the nicotinic cholinergic anti-inflammatory pathway). In particular, described herein are systems and method adapted to increase the duration between stimulations ("off time") while sustaining and even increasing the duration of equivalent inhibition.

BACKGROUND

Electrical stimulation of the neural cholinergic anti-inflammatory pathway (CAP or NCAP) has been described in the literature, beginning with the seminal work of Kevin Tracey (see, e.g., Tracey, K J "Physiology and immunology of the cholinergic antiinflammatory pathway." The Journal of clinical investigation 2007:117 (2): 289-96), who first identified the cholinergic anti-inflammatory pathway and characterized the link between vagus nerve stimulation and inhibition of inflammation by suppressing cytokine production. Since then, research as continued to explore the relationship between stimulation of the CAP and modulation of inflammatory disorders. Typical stimulation parameters have include stimulation by a burst of pulses (e.g., between 10 Hz to 1 GHz for between 30 sec and 20 min), with a slight increase in effect seen at higher frequencies (see, e.g., U.S. Publication No. 2009/0143831 to Huston et al.).

Although this work has suggested that chronic inflammation may be successfully treated by an implantable stimulator, the design and implementation of such a chronically implantable and usable stimulator has proven elusive, in part because of the power demands that a device capable of truly long-term, chronic, usage would face.

Implantable electrical stimulation devices have been developed for therapeutic treatment of a wide variety of diseases and disorders. For example, implantable cardioverter defibrillators (ICDs) have been used in the treatment of various cardiac conditions. Spinal cord stimulators (SCS), or dorsal column stimulators (DCS), have been used in the treatment of chronic pain disorders including failed back syndrome, complex regional pain syndrome, and peripheral neuropathy. Peripheral nerve stimulation (PNS) systems have been used in the treatment of chronic pain syndromes and other diseases and disorders. Functional electrical stimulation (FES) systems have been used to restore some functionality to otherwise paralyzed extremities in spinal cord injury patients.

Recently, implantable vagus nerve stimulations have been developed, including vagus nerve stimulators to treat inflammation. Such implants typically require an electrode and a power source. The size and use-limiting parameters may typically be the power requirements, which either require a long-lasting (and therefore typically large) battery, or require the added complication of charging circuitry and charging devices.

For example, typical implantable electrical stimulation systems may include one or more programmable electrodes on a lead that are connected to an implantable pulse generator (IPG) that contains a power source and stimulation circuitry. Even relatively small implantable neural stimulator technology, i.e. microstimulators, having integral electrodes attached to the body of a stimulator may share some of these disadvantages, as the currently developed leadless devices tend to be larger and more massive than desirable, making it difficult to stably position such devices in the proper position with respect to the nerve.

We herein describe the surprising result that long-lasting, robust inhibition of inflammation may be achieved by on a single (or very few) supra-threshold electrical pulse applied to the vague nerve. This finding is particularly surprising given the extraordinarily robust effect despite the minimal power applied, particularly compared to published data showing effects at much higher applied energy. These findings support various extremely low-power devices, system and methods for treating chronic inflammation. In particular, devices and methods for the treatment of inflammatory disorders, including inflammatory disorders of the intestine (e.g., irritable bowel disorder or IBD) are described, including microstimulators and methods of using them based on the remarkably low power requirements identified.

SUMMARY OF THE DISCLOSURE

Described herein are devices, systems and methods for the extraordinarily low duty cycle stimulation of the vagus nerve. An extraordinarily low, extremely low, super low, or ultra low duty cycle refers generally to a duty cycle that provides stimulation using both a low number of electrical pulses per time period and a low stimulation intensity such that power requirements of the duty cycle are very low. The following are examples of various embodiments of extraordinarily low, extremely low, super low, or ultra low duty cycles. In some embodiments, the number of electrical pulses can be between 1 and 5, in one pulse increments, every 4 to 48 hours (or every 48-72 hours, or ever 2-4 days, or every 2-5 days, or every 2-10 days, or every 2-14 days or every 2-18 days, or every 2-20 days or every 2-25 days, etc.), including in 4 hour increments. In some embodiments, the stimulation intensity can be at a supra-threshold level that is capable of effecting the desired physiological response through the vagus nerves. In some embodiments, the supra-threshold level is between about 100 µA and 5000 µA, or between about 100 µA and 4000 µA, or between about 100 µA and 3000 µA, or between about 100 µA and 2000 µA. In some embodiments, the supra-threshold level is less than about 2000 µA, 3000 µA, 4000 µA or 5000 µA.

In some embodiments, the duty cycle is one supra-threshold pulse every 4 hours, with the pulse amplitude less than about 2000 µA. In some embodiments, the duty cycle is one pulse every 4 hours, with the pulse amplitude less than about 3000 µA. In some embodiments, the duty cycle is one pulse every 12 hours, with the pulse amplitude less than about 2000 µA. In some embodiments, the duty cycle is one pulse every 12 hours, with the pulse amplitude less than about 3000 µA. In some embodiments, the duty cycle is one pulse every 24 hours, with the pulse amplitude less than about 2000 µA. In some embodiments, the duty cycle is one pulse every 24 hours, with the pulse amplitude less than about 3000 µA. In some embodiments, the duty cycle is one pulse every 48 hours, with the pulse amplitude less than about 2000 µA. In some embodiments, the duty cycle is one pulse every 48 hours, with the pulse amplitude less than about 3000 µA.

In some embodiments the pulse width can be between about 100 to 1000 µS, or can be about or less than about 100, 200, 300, 400, 500, 600, 700, 800, 900 or 1000 µS. In some embodiments, the frequency can be about or less than about 10, 20, 30, 40, 50, 60, 70, 80, 90 or 100 Hz. In some embodiments, the IPI can be about or less than about 100, 200, 300, 400, 500, 600, 700, 800, 900 or 1000 µS.

In some embodiments, a system for treating chronic inflammation and/or an inflammatory disorder in a subject is provided. The system includes an implantable microstimulator configured to apply a low duty-cycle stimulation to a vagus nerve, wherein the low duty-cycle stimulation provides no more than a single supra-threshold pulse every four hours; and a controller configured to set a dose for the microstimulator wherein the dose comprises the single supra-threshold pulse followed by an off-period of at least four hours. In some embodiments, the off-period is at least 24 hours, or at least 48 hours, or between about 4 to 48 hours, or between about 12 to 48 hours, or between about 24 to 48 hours. In some embodiments, the single supra-threshold pulse has a pulse amplitude of less than 5 mA, less than 3 mA, or less than 2 mA. In some embodiments, the single supra-threshold pulse is biphasic. In some embodiments, the chronic inflammation is intestinal inflammation. In some embodiments, the chronic inflammation is inflammatory bowel disease. In some embodiments, the chronic inflammation is Crohn's disease.

In some embodiments, a method of treating chronic inflammation and/or inflammatory disorders in a subject is provided. The method includes implanting a microstimulator; and applying only a single supra-threshold stimulus pulse from the microstimulator to the vagus nerve followed by an off-time of at least 4 hours. In some embodiments, the off-time is at least 24 hours, at least 48 hours, or between about 4 to 48 hours, or between about 12 to 48 hours, or between about 24 to 48 hours. In some embodiments, the single supra-threshold stimulus pulse has a pulse amplitude of less than 5 mA, less than 3 mA, or less than 2 mA. In some embodiments, the single supra-threshold stimulus pulse is biphasic. In some embodiments, the chronic inflammation is intestinal inflammation. In some embodiments, the chronic inflammation is inflammatory bowel disease. In some embodiments, the chronic inflammation is Crohn's disease.

Types of inflammatory disorders that may be treated as described herein include a variety of disease states, including diseases such as hay fever, atherosclerosis, arthritis (rheumatoid, bursitis, gouty arthritis, polymyalgia rheumatic, etc.), asthma, autoimmune diseases, chronic inflammation, chronic prostatitis, glomerulonephritis, nephritis, inflammatory bowel diseases, pelvic inflammatory disease, reperfusion injury, transplant rejection, vasculitis, myocarditis, colitis, etc.

Non-limiting examples of inflammatory disorders which can be treated using the present invention include appendicitis, peptic ulcer, gastric ulcer, duodenal ulcer, peritonitis, pancreatitis, ulcerative colitis, pseudomembranous colitis, acute colitis, ischemic colitis, diverticulitis, epiglottitis, achalasia, cholangitis, cholecystitits, hepatitis, Crohn's disease, enteritis, Whipple's disease, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, pneumonitits, pneumoultramicroscopic silicovolcanoconiosis, alvealitis, bronchiolitis, pharyngitis, pleurisy, sinusitis, influenza, respiratory syncytial virus infection, HIV infection, hepatitis B virus infection, hepatitis C virus infection, herpes virus infection disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thyroiditis, systemic lupus erythematosis, Goodpasture's syndrome, Behcet's syndrome, allograft rejection, graft-versus-host disease, Type I diabetes, Type II diabetes, ankylosing spondylitis, Berger's disease, Reiter's syndrome, Hodgkin's disease, ileus, hypertension, irritable bowel syndrome, myocardial infarction, sleeplessness, anxiety and stent thrombosis.

The systems and methods described herein generally relate to systems and devices for treatment of chronic inflammation and inflammatory disorders. In particular, described herein are systems, devices and methods for treating intestinal disorders and rheumatoid arthritis. Further described herein generally are methods and devices, including an implantable microstimulators, adapted for electrically stimulating the vagus nerve to treat chronic inflammation by extremely- or super-low duty cycle stimulation and by extremely low treatment dose schedule to modulate an inflammatory response (via the cholinergic anti-inflammatory pathway).

For example, any of the systems and methods described herein may include or be specifically adapted and/or configured to deliver a treatment regimen in which the delay between stimulation doses (including single bursts and/or single pulses of supra-threshold stimulation) is progressively increased from the start of stimulation so that subsequent (later) stimulation occurs with longer off-times than earlier doses, without substantially decreasing the inhibition of inflammation due to the vagal stimulation. This effect may be referred to herein as 'training' the subject or vagus nerve, as the later stimulation (following an initial training period) may achieve the same or even more robust inhibition of inflammation with a longer duration between applied vagal stimulation. In general, the effect of VNS stimulation described herein may be referred to as an inhibition of the inflammatory response, and may include the inhibition of cytokines, or the increase of anti-inflammatory cytokines, or both.

For example, described herein are systems for treating chronic inflammation in a subject that include: an implantable microstimulator configured to apply a low duty-cycle stimulation to a vagus nerve; and a controller adapted to set a dose regimen of progressively delayed supra-threshold stimulus pulses for the microstimulator, wherein the dose regimen comprises a first dose comprising a supra-threshold stimulus pulse followed by a first off-period of at least about 48 hours, a second dose comprising a supra-threshold stimulation pulse followed by a second off-period that is longer than the first off-period, and a series of sequential doses each comprising a supra-threshold stimulation pulse followed by an off-period that is longer than the second off-period, wherein the supra-threshold stimulus pulses are configured to reduce a level of inflammation in the subject.

The first off-period is may be least about 72 hours, or 3.5 days, 4 days, 5 days, 6 days or 7 days, etc., and the second off period may be at least about 1.1 to 3 times the first off period (e.g., 5 days, 6 days, 7 days, 8 days, 9 days, 10 days, 11 days, 12 days, 13 days, 14 days, etc.). For example, the second and/or subsequent off-periods may be between about 1.1 and 2 times the first off period (e.g., 1.2 and 2.2 times, etc.). In one example, illustrated below, the first off-period is about 7 days and the second off period is at least about 10 days. In general, the off-period is the quiescent period during which no supra-threshold (and/or no stimulation at all) is applied by the implant to the vagus. In general, the time of the first off period may be determined based on the amount of inhibition of inflammation. For example, the duration of the first off period and subsequent off periods may be determined by examining the level of inhibition of inflammation (of an inflammatory response) or of a marker for inflammation and/or the inflammatory response. For example, the off-period may extend until inflammation or a marker for inflammation and/or the inflammatory response (either ongoing or evoked from the subject) is a percentage of the native inflammation level or inflammatory response (e.g., above about 30%, 40%, 50%, 60%, 70%, 75%, 80%, 85%, 90%, 95%), etc. Thus, for example, the off-periods of the sequential doses may each at least about two weeks. In some variations, the off-periods of the sequential doses are ramped up to a predetermined length of time. Thus, for example, the second off-period may be longer than the first off-period and subsequent off-periods may be longer still (progressively longer), but may approach a limit (e.g., of two weeks, 18 days, 3 weeks, 25 days, etc.). The limit may be a maximum delay period. In general, in the methods and apparatuses described herein, the application of the ultra-low duty-cycle stimulation at the progressive off-times described herein may result in a tonic (ongoing) inhibition of inflammation (or of markers for inflammation) at an acceptable level. This may permit remarkably low-power (or low-power consumption) devices that may be operated for many days, weeks or even months, without requiring power replacement or recharging while maintaining efficacy.

As mentioned above, the first dose may comprise a single supra-threshold stimulus pulse, or burst of pulses. A burst of pulses typically has a burst duration of less than about 5 minutes, less than about 4 min, 3 min, 2 min, 1 min, etc.). One or more (including all) of the pulses in the burst may be supra threshold. In some variations, for example, the dose (including the first dose) comprises a single burst of supra-threshold stimulus pulses.

Any of the devices and methods described herein may be configured to sense an indicator of the subject's inflammation or inflammatory response. For example, a system may include an analyte detector configured to measure a level of an inflammatory analyte in the subject's blood or bodily fluids (e.g., the level of a marker of an inflammatory response). Some variations may include a sensor configured to detect a measure of inflammation based on the electrical activity of the vagus nerve; thus any of these systems may include one or more electrodes to sense activity on the vagus nerve. In any of these systems, the system (e.g., the controller) may be configured to adjust the doses (e.g., the second dose and/or subsequent doses) based on the level of inflammation in the subject, e.g., the level of inhibition of inflammation in the subject. For example, a controller may be configured to adjust the second dose and subsequent doses based on the level of an inflammatory analyte, and/or the controller may be configured to adjust the second off-period based on the level of inflammation in the subject (e.g. the level of the inhibition of the inflammatory response).

The controller may be configured to adjust the second off period based on the level an inflammatory analyte, e.g., based on the amount of inhibition of the inflammatory response. As mentioned, the microstimulator may include a sensing electrode configured to monitor vagus nerve activity; this activity may be analyzed (e.g., by the microstimulator or remotely from the microstimulator, which may transmit and receive data and/or command information or instructions). The microstimulator may comprise a sensing electrode configured to monitor vagus nerve activity, and also a processor configured to process the monitored vagus nerve activity to determine a level of inflammation and/or the level of inhibition of inflammation.

Also described herein are methods of treating chronic inflammation in a patient by progressively increasing the off-times between stimulation. For example, a method may include: applying a single supra-threshold stimulus from a microstimulator to a vagus nerve, wherein the delivery of the stimulus is followed by a first off-time of at least about 48 hours during which an inflammatory response is suppressed; and applying subsequent supra-threshold stimuli, wherein each subsequent stimulus is followed by an off-time of longer than 48 hours.

The step of applying the single supra-threshold stimulus may include applying a single burst of pulses, or a single supra-threshold pulse. As mentioned above, the off-times may be predetermined as part of the dosing regimen (e.g., the first off-time may at least about 72 hours, 4 days, 5 days, 6 days, 7 days, etc.). The first off-time may be, for example, at least about 7 days. The subsequent off-times may be predetermined and/or may be modified by one or more subject-specific parameters, including, for example, the level of inhibition of the inflammatory response for the subject. For example, after the first or second stimulation doses are applied, the subsequent off-times may be at least about one to two weeks. As mentioned, the subsequent off times may be ramped up from the first off-time to a longer predetermined length of time (e.g., up to two weeks, 2.5 weeks, three weeks, 3.5 weeks, four weeks, etc.).

In any of these variations, the method may include a step of determining the level of inflammation (or the level of inhibition of the inflammatory response) and adjusting the off-times following the subsequent supra-threshold stimuli based on the level of inflammation and/or the level of inhibition of the inflammatory response. For example, the level of inflammation and/or inhibition of inflammation may be estimated by monitoring vagus nerve activity; the off-times following the subsequent supra-threshold stimuli may be adjusted based on the level of inflammation and/or the level of inhibition of inflammation.

In general, any of these methods may also include determining the level of an inflammatory analyte in the subject's blood or bodily fluids and adjusting the off-times following the subsequent supra-threshold stimuli based on the level of analyte. The level of the analyte may be indicative of the level of inflammation and/or the level of inhibition of inflammation. For example, a level of inhibition of inflammation may be determined by comparison to a baseline (e.g., prior to vagus nerve stimulation as described). The level of inhibition of inflammation may be determined as a percentage of inhibition of this inflammatory response. The inflammatory response may be determined by evoking (e.g., ex vivo or in vivo) an inflammatory response and comparing it to a current (or some post-stimulation) time point.

Also described herein are methods of treating chronic inflammation in a subject by progressively increasing the off-times between stimulation. For example, a method may comprise: applying to a vagus nerve from an implanted microstimulator, a first dose comprising a supra-threshold stimulus, followed by a first off-time of at least about 48 hours, wherein the application of the first dose reduces the level of inflammation in the subject; applying a second dose comprising a supra-threshold stimulus, followed by a second off-time that is longer than the first off-time; and applying subsequent doses comprising supra-threshold stimuli, wherein each does is followed by an off-time that is longer than the second off-time.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
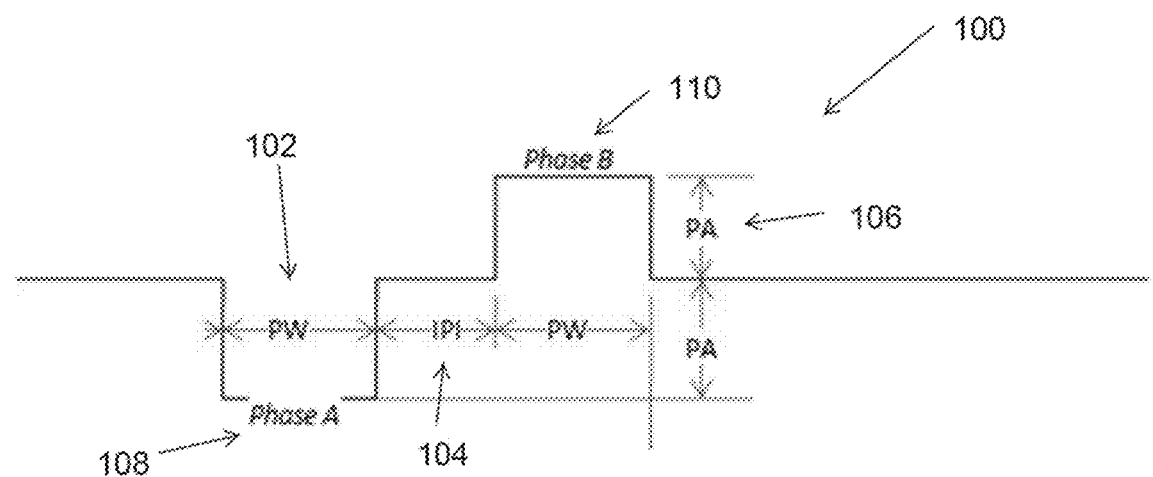
FIG. 1 is a diagram of a single stimulation waveform.

In general, described herein are systems, methods and devices illustrating extraordinarily low duty cycle stimulation of the vagus nerve to treat a disorder. In particular, described herein are systems, methods and devices illustrating extraordinarily low duty cycle stimulation of the vagus nerve to reduce or prevent inflammation and the effects of inflammation in a mammalian model. An extraordinarily low, extremely low, super low, or ultra low duty cycle refers generally to a duty cycle that provides stimulation using both a low number of electrical pulses per time period and a low stimulation intensity such that power requirements of the duty cycle are very low. The methods described herein apply various stimulation protocols that may be used to significantly reduce inflammation and/or the effects of inflammation. Simulation parameters that may be varied include the pulse shape (e.g., sinusoidal, square, biphasic, monophasic, etc.) the duration of stimulation, the on-time, the off-time, the inter-pulse interval, or the like. One key factor examined herein is the number of supra-threshold pulses. As shown herein, the stimulation of the vagus nerve with even a single supra-threshold stimulus results in a significant and long-lasting effect, even when compared to multiple stimulations. This effect was particularly profound when examined using a rodent model for IBD.

The following are examples of various embodiments of extraordinarily low, extremely low, super low, or ultra low duty cycles. In some embodiments, the number of electrical pulses can be between 1 and 5, in one pulse increments, every 4 to 48 hours, in 4 hour increments. In some embodiments, the stimulation intensity can be at a supra-threshold level that is capable of effecting the desired physiological response through the vagus nerves. In some embodiments, the supra-threshold level is between about 100 µA and 5000 µA, or between about 100 µA and 4000 µA, or between about 100 µA and 3000 µA, or between about 100 µA and 2000 µA. In some embodiments, the supra-threshold level is less than about 2000 µA, 3000 µA, 4000 µA or 5000 µA.

In some embodiments, the duty cycle is one supra-threshold pulse every 4 hours, with the pulse amplitude less than about 2000 µA. In some embodiments, the duty cycle is one pulse every 4 hours, with the pulse amplitude less than about 3000 µA. In some embodiments, the duty cycle is one pulse every 12 hours, with the pulse amplitude less than about 2000 µA. In some embodiments, the duty cycle is one pulse every 12 hours, with the pulse amplitude less than about 3000 µA. In some embodiments, the duty cycle is one pulse every 24 hours, with the pulse amplitude less than about 2000 µA. In some embodiments, the duty cycle is one pulse every 24 hours, with the pulse amplitude less than about 3000 µA. In some embodiments, the duty cycle is one pulse every 48 hours, with the pulse amplitude less than about 2000 µA. In some embodiments, the duty cycle is one pulse every 48 hours, with the pulse amplitude less than about 3000 µA.

The examples described herein use a stimulator and stimulation control package that was developed for use in driving vagus nerve stimulation. In some example, the stimulation is controlled by a software package that is configured to run on a microprocessor (e.g., personal computer) and to control output of an emulator/stimulator (which may be referred to as an "ITE" or integrated terminal emulator). Thus, the systems described herein may include logic (e.g., control logic) that may be software, firmware, and/or hardware to control the application of stimulation. For example, in some variations, the parameters controlling stimulation and data acquisition may include: (1) selected stimulating electrode pair including a cathode and anode; (2) frequency in 1 Hz increments; (3) Pulse Width (PW): 20-2,000 uS in 1 uS increments; (4) Pulse Amplitude (PA): ±0-5,000 uA in 3 uA increments; and (5) Inter-Pulse-Interval between phase A & B of waveform (IPI): 20-2,000 uS in 1 uS increments.

In addition to the exemplary parameters provided above, in some embodiments the PW can be between about 100 to 1000 µS, or can be about or less than about 100, 200, 300, 400, 500, 600, 700, 800, 900 or 1000 µS. In some embodiments, the frequency can be about or less than about 10, 20, 30, 40, 50, 60, 70, 80, 90 or 100 Hz. In some embodiments, the IPI can be about or less than about 100, 200, 300, 400, 500, 600, 700, 800, 900 or 1000 µS.

For example, the exemplary waveform shown on FIG. 1 is a biphasic (charge balanced) waveform 100 that includes two symmetric pulse widths 102 (PW) separated by an inter-pulse interval 104 (IPI). The pulse widths 102 have a pulse amplitude 106 (PA) that is also symmetric for the first phase 108 (phase A) and the second phase 110 (phase B) of the biphasic stimulus, with a negative pulse amplitude in phase A and a positive amplitude in phase B. This biphasic pulse is a single pulse that includes both a positive and negative excursion. Other pulse waveforms may be used. In some embodiments, the pulse waveforms may be non-biphasic and/or may have asymmetric pulse widths and/or asymmetric pulse amplitudes.

The stimulator may generate a pulse train on a pair of electrodes. In general, a does may include a single pulse (e.g., a single biphasic pulse) or a single burst including multiple pulses. The pulses may be generated using a bipolar current source and can be capacitively isolated with >1 uF ceramic capacitors on both electrodes outputs. Compliance voltage can be set to as high as +/−18.8 volts.

The different experimental examples described herein show that appropriate NCAP stimulation of the vagus nerve can be used to limit or eliminate the effects of intestinal inflammation, in particular in a rat model of colitis and a rat model of Crohn's disorder. Based on this data, a biphasic simulation at the parameters described above may successfully treat intestinal inflammation in humans or other mammals.

Figure 2:
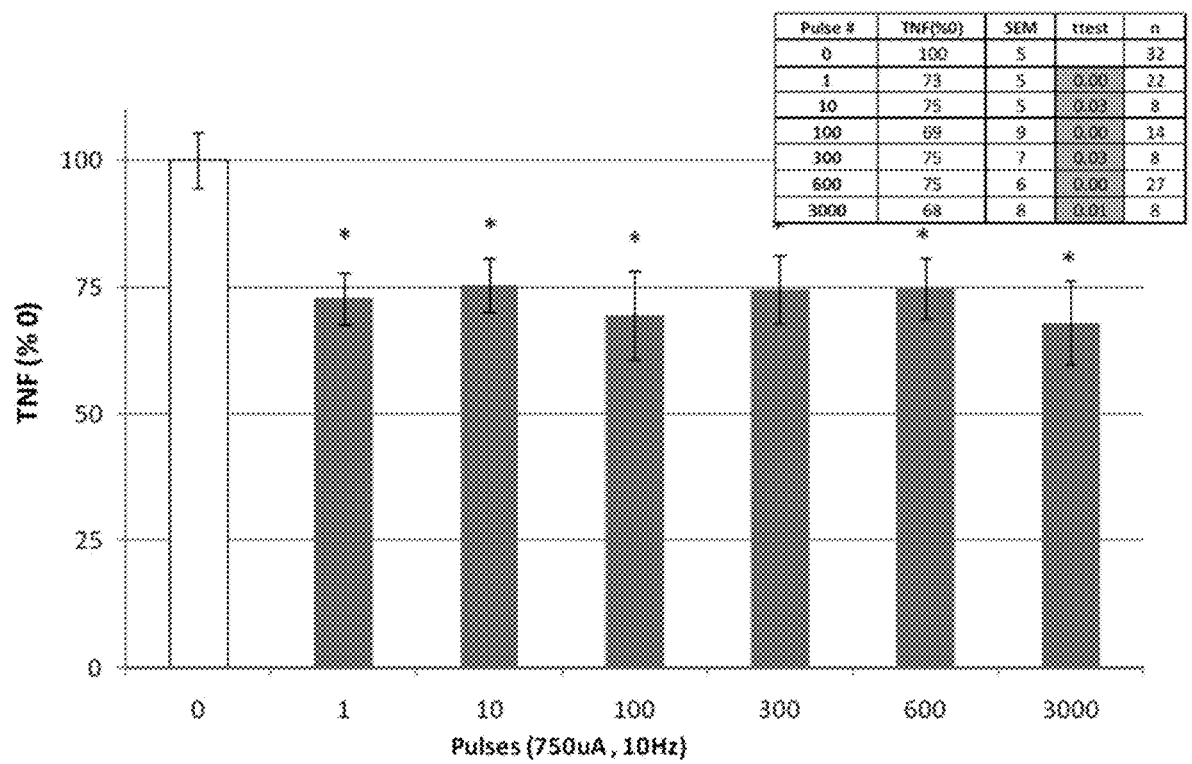
FIG. 2 is a graph comparing the effect on TNF levels from a single stimulation pulse with the effect from up to 3000 pulses.

In one example, mice (Male, BALB/c) were anesthetized and cuff electrodes (0.3 mm ID, 0.5 mm inter-electrode distance; Microprobes, Gaithersburg, MD) were placed around the left carotid sheath (containing the cervical vagus nerve) and secured by suture. Supra-threshold pulses (750 µA, 200 µS, 10 Hz) were applied in various numbers (0, 1, 10, 100, 300, 600, 3000). Afterwards, the electrode was removed and the wound stapled closed. Mice recovered for 3 hours, and then were challenged with LPS (5 mg/kg; IP); these mice were sacrificed 90 minutes post-LPS and serum TNF measured by ELISA to measure the effects on inflammatory cytokines. As shown on FIG. 2, even a single supra-threshold stimulus resulted in a significant suppression of TNF at 3 hours after treatment. Thus, the effect was long lasting and the effect from a single pulse at 3 hours was equivalent to the effect generated by up to 3000 pulses.

Figure 3:
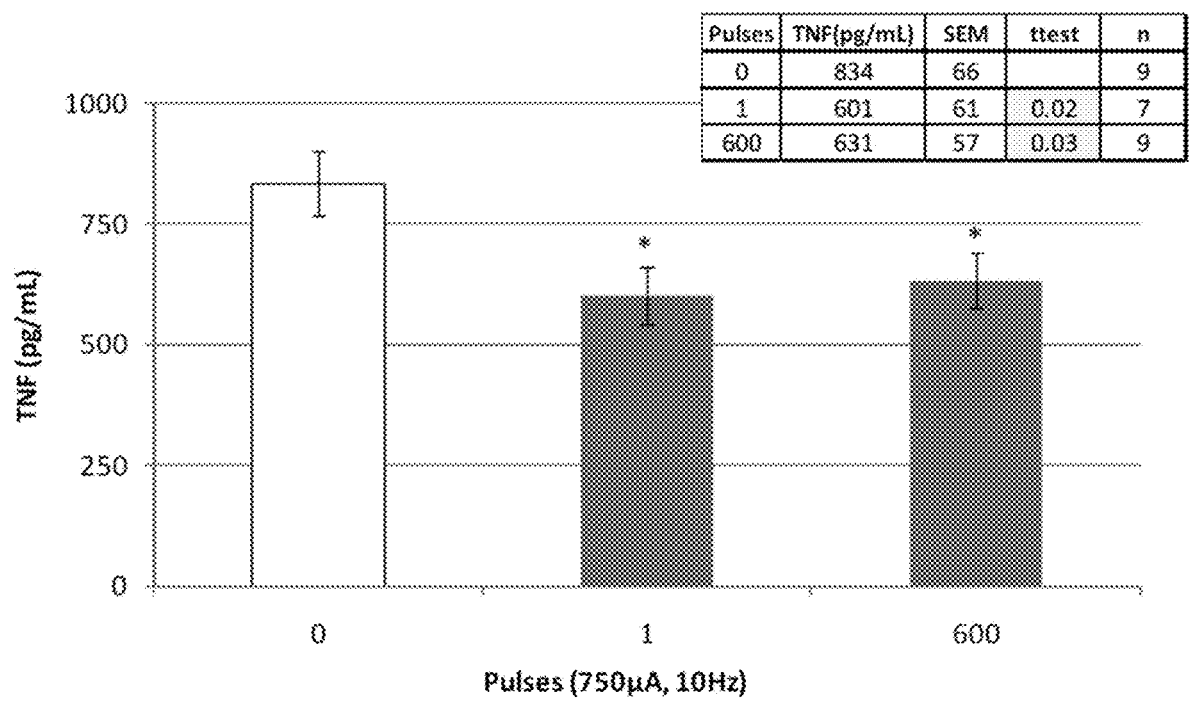
FIG. 3 is a graph illustrating the effect on TNF levels from a single stimulation pulse 24 hours post-stimulation.

A second similar experiment was conducted to examine the long lasting effect of a single supra-threshold pulse on the cholinergic anti-inflammatory pathway (CAP). Mice (Male, BALB/c) were anesthetized and cuff electrodes (0.3 mm ID, 0.5 mm inter-electrode distance; Microprobes, Gaithersburg, MD) were placed around the left carotid sheath (containing the cervical vagus nerve) and secured by suture. Supra-threshold pulses (750 µA, 200 µS, 10 Hz) were applied in various numbers (0, 1, 600). Afterwards, the electrode was removed and the wound stapled closed. Mice recovered for 24 hours, and then were challenged with LPS (5 mg/kg; IP); these mice were sacrificed 90 minutes post-LPS and serum TNF measured by ELISA to measure the effects on inflammatory cytokines. As shown on FIG. 3, a single supra-threshold stimulus resulted in a significant suppression of TNF at 24 hours after treatment that was equivalent to the effect generated by 600 pulses.

Figure 4:
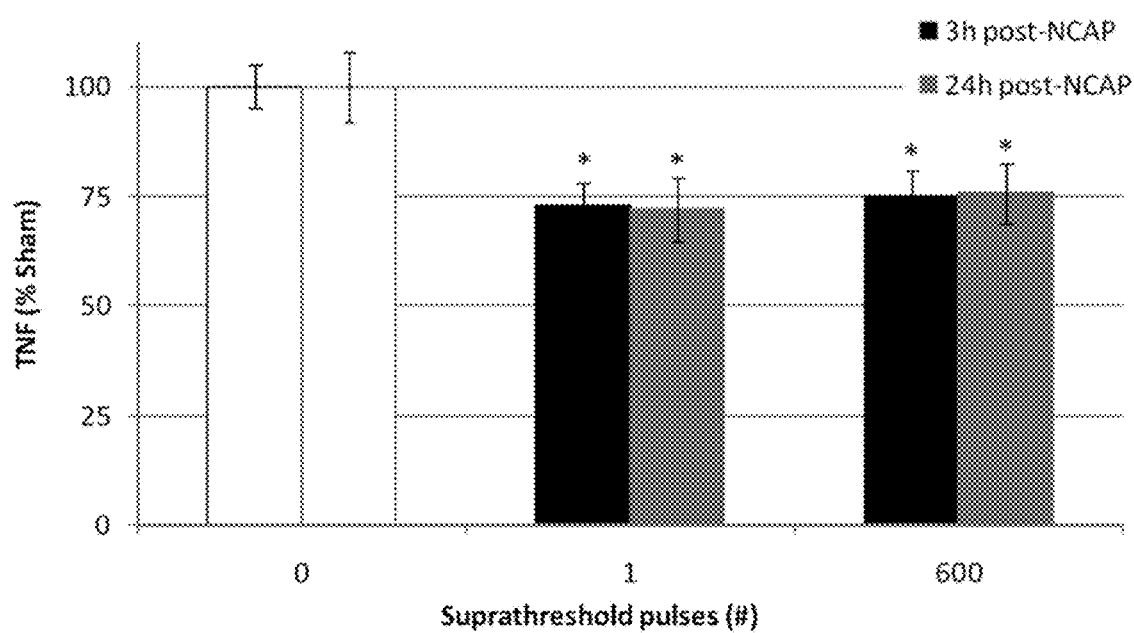
FIG. 4 is a graph illustrating the effect on TNF levels from a single stimulation pulse 3 hours and 24 hours post-stimulation.

FIG. 4 combines selected portions of the results of the two experiments described above to show that single pulse stimulation of the NCAP effects suppression of LPS-inducible TNF at 3 hours and 24 hours post-stimulation at the same effectiveness as 600 pulses.

Figure 5:
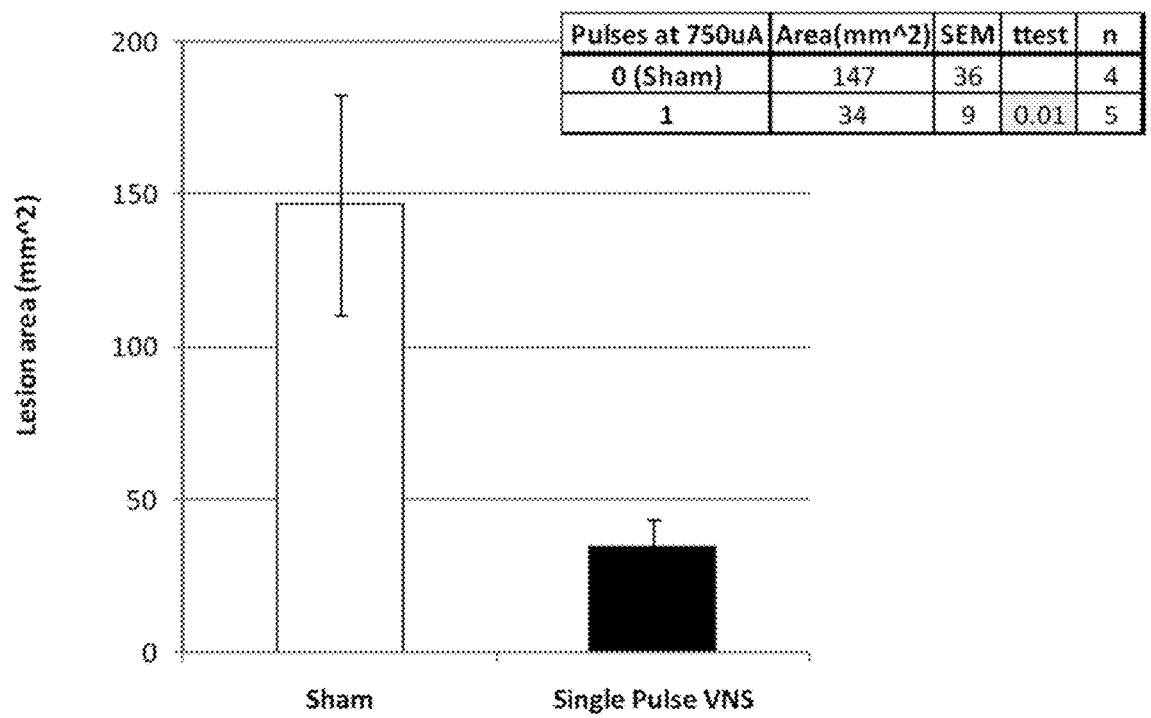
FIG. 5 is a graph illustrating the effect on lesion area in a rat model of IBD from a single stimulation pulse.

In another example, an experiment was conducted to determine the effectiveness of single pulse suppression of lesion area in a rat model for IBD/Crohn's disease. Rats were anesthetized and were either given a sham stimulation or a single supra-threshold stimulus to the left cervical vagus nerve (1 pulse at 750 µA, 200 µS pulse width, 10 Hz). IBD was induced at 30 minutes post-stimulation by the SC injection of indomethacin (10 mg/kg (5 mg/mL) in 5% sodium bicarbonate). Lesions were stained in-life 23.5 hours post-indomethacin injection by anesthetizing the rats with isoflurane and IV tail injection with Evans Blue (0.3 ml of 1%). Rats were sacrificed via C02 asphyxiation at 24 hours post disease induction, and the small intestines were harvested, cleaned and fixed in 2% formalin overnight. Photographs were taken and digitized of the fixed intestines and lesions were quantified by a blinded scorer. As illustrated in FIG. 5, a single supra-threshold stimulus (750 µA, 200 µS pulse width, 10 Hz) resulted in a profound reduction in lesions.

Figure 6:
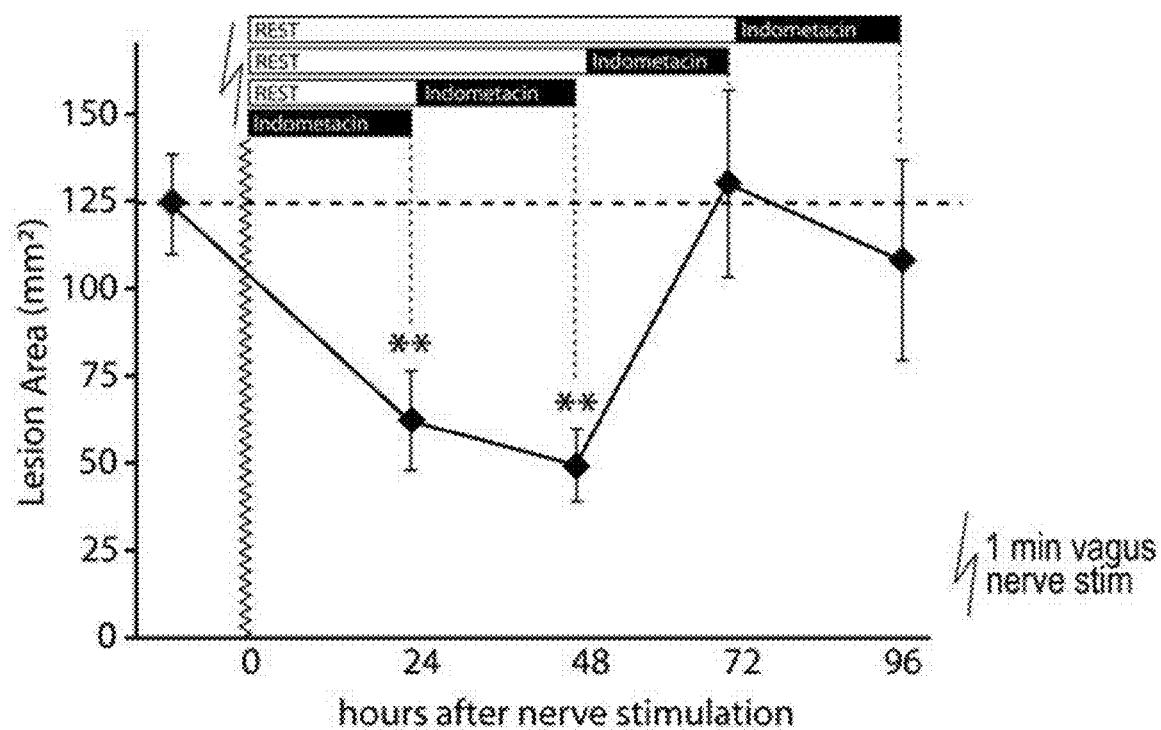
FIG. 6 is a graph illustrating the long term effect on lesion area in a rat model of IBD from a single stimulation pulse.

These results are even more significant, given the data shown in FIG. 6, which illustrates a "memory effect" of vagus nerve stimulation in a rat model of Crohn's disease. Rats were anesthetized and were either given a sham stimulation or an actual stimulation to the left cervical vagus nerve (1 mA, 200 µS pulse width, 10 Hz, 60 s). IBD/Crohn's disease was induced at various times (see FIG. 6) post-stimulation by the SC injection of indomethacin (10 mg/kg (5 mg/mL) in 5% sodium bicarbonate). Lesions were stained in-life 23.5 hours post-disease induction by anesthetizing the rats with isoflurane and IV tail injection with Evans Blue (0.3 ml of 1%). Rats were sacrificed via $CO_2$ asphyxiation at 24 hours post disease induction, and the small intestines were harvested, cleaned and fixed in 2% formalin overnight. Photographs were taken and digitized of the fixed intestines and lesions were quantified by a blinded scorer. In this example, a brief period of stimulation of the vagus nerve may result in a surprisingly long-lasting effect (e.g., up to 48 hours) in the reduction of intestinal lesions otherwise induced by the application of indomethacin. This data strongly suggests that stimulation may be provided extremely infrequently, with long (e.g., >48 hours) of "silent" periods without stimulation applied. Such extremely low duty-cycle stimulation for treating IBD may be particularly helpful in implantable systems, allowing extremely long battery life while having unexpectedly robust therapeutic benefits.

Although the examples provided above describe methods, systems and devices for treating an inflammatory disorder in a rat model, all the methods, systems and devices described herein can be used and/or adapted for use in other mammals, such as humans. For example, a system and method for treating an inflammatory disorder in a human using a single supra-threshold pulse and/or an extraordinarily low duty cycle stimulation protocol can include an electrode, such as a cuff electrode, that is configured to be implanted around the vagus nerve and deliver electrical stimulation to the vagus nerve of the subject. The system can further include a processor, memory for storing instructions, and/or a controller can include programming to deliver the low duty cycle stimulation protocol, including the single supra-threshold pulse protocol, to the vagus nerve via the cuff electrode. A battery can be provided to provide power for the system, and because the low duty cycle stimulation protocol consumes so little energy, the battery life can be greatly extended, allowing the system to be completely implanted within the subject for a long duration before the battery needs to be replaced or recharged. For an implanted system, this provides a great benefit since it can reduce the frequency of surgical procedures that may be required to change the battery.

The stimulation parameters used in this system can be the same or similar to the parameters disclosed above. For example, the pulse amplitude can be less than about 5, 4, 3, or 2 mA. In addition, the low duty cycle stimulation protocol can deliver a single supra-threshold pulse between off-times of between about 4 to 48 hours, or at least 4, 12, 24, or 48 hours. In some embodiments the pulse width can be between about 100 to 1000 µS, or can be about or less than about 100, 200, 300, 400, 500, 600, 700, 800, 900 or 1000 µS. In some embodiments, the frequency can be about or less than about 10, 20, 30, 40, 50, 60, 70, 80, 90 or 100 Hz. In some embodiments, the IPI can be about or less than about 100, 200, 300, 400, 500, 600, 700, 800, 900 or 1000 µS.

In general, these results suggest that the application of even a single brief supra-threshold stimulus of the vagus nerve may result in a substantial reduction in the effects of inflammation, possibly by inhibition of inflammatory cytokines such as TNF. These results are both surprising, given the prior arts tendency to stimulate for much longer times, and important for the design of future devices and methods. In particular, stimulation of the vagus nerve (or other portions of the inflammatory reflex) may be configured to apply extremely low duty-cycle stimulation. As mentioned briefly, this would allow for much smaller, lighter and more efficient implantable stimulation systems.

Another phenomenon seen in the experiments of FIGS. 2-7 is the training effect in which subsequent vagus nerve stimulation, particularly with extremely low duty-cycle stimulation, results in increasing the duration of suppression of the inflammatory response in the patient. For example, in mice, as well as other mammals into which a microstimulator has been applied to the vagus nerve, the first application of a dose of a dosing regimen (and particularly an extremely low duty-cycle dose), e.g., a since burst of supra-threshold pulses, e.g., having a burst duration of less than 5 min, 2 min, 1 min, etc., or even a single supra-threshold pulse, results in an inhibition of inflammation that lasts for many hours, and even days, as shown in FIG. 6. A second dose (e.g., pulse of supra-threshold stimulation) that is equivalent to the first pulse results in a longer-lasting inhibition than the first dose. Subsequent stimulation may also result in longer-lasting inhibition than preceding simulation. This means that the off-period between stimulation may be increased with subsequent stimulation, as is seen, for example, in FIGS. 9 and 10, discussed below. Preliminary data suggests that the lower duty-cycle (e.g., single pulse/single burst of limited burst duration) stimulation may be most effective in creating this enhanced duration of inhibition. When multiple (e.g., greater than 100 supra-threshold pulses, greater than 90 supra-threshold pulses, greater than 80 supra-threshold pulses, greater than 70 supra-threshold pulses, greater than 60 supra-threshold pulses, greater than 50 supra-threshold pulses, greater than 40 supra-threshold pulses, greater than 30 supra-threshold pulses, greater than 25 supra-threshold pulses, greater than 20 supra-threshold pulses, etc.) are used, significant enhancement of the duration of inhibition may not be robustly observed. Thus, it may be beneficial to limit the number of pulses in dose to less than 100, 90, 80, 70, 60, 50, 40, 30, 25, 20 etc. supra-threshold pulses, separated by an off-time of greater than 48 hours, 3 days, 4, days, etc.

Types of inflammatory disorders that may be treated as described herein include a variety of disease states, including diseases such as hay fever, atherosclerosis, arthritis (rheumatoid, bursitis, gouty arthritis, polymyalgia rheumatic, etc.), asthma, autoimmune diseases, chronic inflammation, chronic prostatitis, glomerulonephritis, nephritis, inflammatory bowel diseases, pelvic inflammatory disease, reperfusion injury, transplant rejection, vasculitis, myocarditis, colitis, etc.

Non-limiting examples of inflammatory disorders which can be treated using the present invention include appendicitis, peptic ulcer, gastric ulcer, duodenal ulcer, peritonitis, pancreatitis, ulcerative colitis, pseudomembranous colitis, acute colitis, ischemic colitis, diverticulitis, epiglottitis, achalasia, cholangitis, cholecystitits, hepatitis, Crohn's disease, enteritis, Whipple's disease, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, pneumonitits, pneumoultramicroscopic silicovolcanoconiosis, alvealitis, bronchiolitis, pharyngitis, pleurisy, sinusitis, influenza, respiratory syncytial virus infection, HIV infection, hepatitis B virus infection, hepatitis C virus infection, herpes virus infection disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thyroiditis, systemic lupus erythematosis, Goodpasture's syndrome, Behcet's syndrome, allograft rejection, graft-versus-host disease, Type I diabetes, Type II diabetes, ankylosing spondylitis, Berger's disease, Reiter's syndrome, Hodgkin's disease, ileus, hypertension, irritable bowel syndrome, myocardial infarction, sleeplessness, anxiety and stent thrombosis.

Any of these disorders (e.g., inflammatory disorders) may be treated by, for example, implanting a cuff electrode around the vagus nerve, and using an extraordinarily low duty cycle stimulation protocol as described herein to treat. A processor and memory for storing instructions and/or programming can be used to control the stimulation protocol. The stimulation parameters used in this system and method can be the same or similar to the parameters disclosed above. For example, the pulse amplitude of the single supra-threshold pulse can be less than about 5, 4, 3, or 2 mA. In addition, the low duty cycle stimulation protocol can deliver a single supra-threshold pulse between off-times of between about 4 to 48 hours, or at least 4, 12, 24, or 48 hours. Any of these methods may include a step of determining the efficacy of the treatment. For example, any of these methods may include the step of monitoring the subject before and/or during treatment. For example, in treating an inflammatory disorder, a biomarker for inflammation may be monitored, such as a cytokine or other marker. In some variations, monitoring the subject may include assessing the subject visually (e.g., for swelling, body temperature, etc.). In some variations the systems described herein may include a sensor and/or data processing subsystem for monitoring the subject and/or the effect of the treatment with the system.

Although the examples and description above focuses primarily on inflammatory disorders, in some embodiment, the systems, devices and methods described herein can be used to treat non-inflammatory diseases or disorders. For example, the systems, devices and methods described herein can be used to activate, regulate, and/or modulate the levels of sirtuins by extraordinarily low duty cycle stimulation of the vagus nerve. The modulation of sirtuins by vagus nerve stimulation is also discussed in U.S. patent application Ser. No. 13/338,185, filed Dec. 27, 2011, titled "MODULATION OF SIRTUINS BY VAGUS NERVE STIMULATION," Publication No. US-2013-0079834-A1 which is hereby incorporated by reference in its entirety for all purposes. As above, a cuff electrode can be implanted around the vagus nerve and a processor and memory for storing instructions and/or programming can be used to control the stimulation protocol. The stimulation parameters used in this system and method can be the same or similar to the parameters disclosed above. For example, the pulse amplitude of the single supra-threshold pulse can be less than about 5, 4, 3, or 2 mA. In addition, the low duty cycle stimulation protocol can deliver a single supra-threshold pulse between off-times of between about 4 to 48 hours, or at least 4, 12, 24, or 48 hours. In some embodiments the pulse width can be between about 100 to 1000 µS, or can be about or less than about 100, 200, 300, 400, 500, 600, 700, 800, 900 or 1000 µS. In some embodiments, the frequency can be about or less than about 10, 20, 30, 40, 50, 60, 70, 80, 90 or 100 Hz. In some embodiments, the IPI can be about or less than about 100, 200, 300, 400, 500, 600, 700, 800, 900 or 1000 µS.

As mentioned above, in some embodiments, the system, device, and/or method includes monitoring the effects of the stimulation on the disease being treated. For example, inflammation indicators or disease indicators or other indicators can be monitored to evaluate the efficacy of the treatment protocol, allowing the stimulation protocol to be adjusted based on the evaluation. Any one of the parameters described herein can be modulated based on the evaluation. For example, the pulse amplitude and/or the off time can be increased or decreased to optimize the treatment efficacy. Examples of indicators that can be monitored include TNF levels, lesion size, degree or level of inflammation, cytokine levels, pain levels, sirtuin levels, and the like.

Another key factor examined herein is the longevity of effect of a single stimulation as well as the increase in the longevity of effect following a second stimulation that is applied after, for example, seven days later. In other embodiments, the second stimulation is delivered between 1-14 days after the first stimulation. In some embodiments, a third stimulation can be delivered 1-30 days after the second stimulation. More generally, the time period between stimulations can be increased after each stimulation until a desired or predetermined period of time between stimulations is achieved. In some embodiments, the time period between stimulations can be predetermined. The predetermined time period between stimulations may be constant, or can increase over time to a predetermined duration. In embodiments where the time period between stimulations is increased over time, the increase can be gradual, stepwise, or based according to a predetermined schedule. For example, the time period can be increased by 5, 10, 15, 20, or 25 percent, or by about 5-25 percent over the previous time period.

In other embodiments, the time period can be based on a measurement of analyte levels, biomarker levels, an assessment of the level of inflammation, and/or level or pattern or signature of vagus nerve activity, such that the next stimulation is applied when the analyte level, biomarker level, assessment of the level of inflammation, and/or level or pattern or signature of vagus nerve activity either exceeds or falls below a predetermined threshold. The levels or presence of analytes and biomarkers can also be indicators for inflammation. For example, the analyte can be TNF or another inflammatory cytokine or mediator. In some embodiments, the inflammatory analyte or biomarker can be measured ex vivo in a whole blood response assay or in another assay using whole blood or blood plasma. The assessment of the level of inflammation can also be a clinical assessment and/or a patient assessment, and can include a measurement and/or scoring of swelling and/or pain. In some embodiments, the measurements and/or assessments can be performed at predetermined intervals, such as daily, or every two days, which can begin immediately or after a predetermined time has elapsed, such as after 1, 2, 3, 4, 5, 6, or 7 days, for example. The level or pattern or signature of vagus nerve activity can also be correlated with levels of inflammation, allowing level of inflammation to be determined by monitoring of vagus nerve electrical activity, which can be done with a microstimulator with electrical sensing leads and signal processing circuitry and/or software, which can be on the microstimulator or on a computing device in communication with the microstimulator. In some embodiments, various combinations of the above can be used to increase the time period between stimulations.

Figure 7:
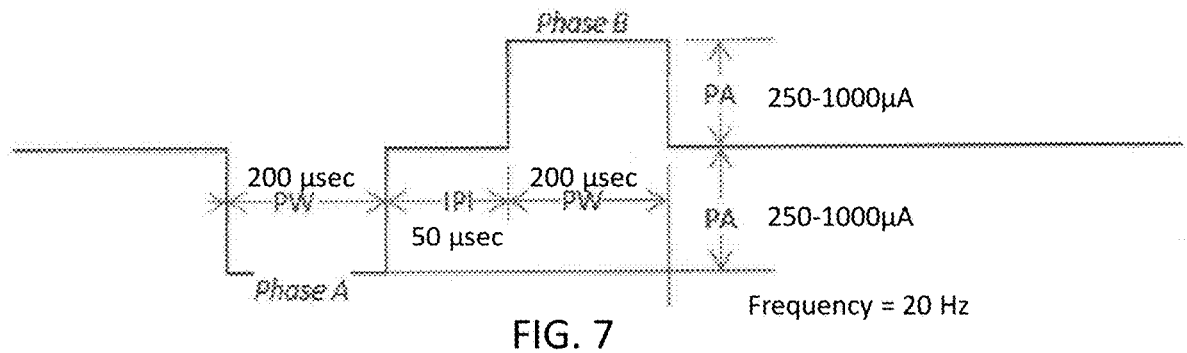
FIG. 7 is a diagram of an embodiment of a stimulation waveform.

The examples described herein may use a stimulator and stimulation control package that was developed for use in driving vagus nerve stimulation. In some examples, the stimulation is controlled by a software package that is configured to run on a microprocessor (e.g., personal computer) and to control output of an emulator/stimulator (which may be referred to as an "ITE" emulator stimulator). With reference to FIG. 7, the parameters controlling stimulation and data acquisition may include: (1) selected stimulating electrode pair including a cathode and Anode; (2) frequency in 1 Hz increments; (3) Pulse Width (PW): 20-2,000 uS in 1 uS increments; (4) Pulse Amplitude (PA): ±0-5,000 uA in 3 uA increments; and (5) Inter-Pulse-Interval between phase A & B of waveform (IPI): 20-2,000 uS in 1 uS increments.

For example, the exemplary waveform shown on FIG. 7 is a biphasic (charge balanced) waveform that includes two symmetric pulse widths (PW, one positive, one negative) separated by an inter-pulse interval (IPI). The pulse widths have a pulse amplitude (PA) that is also symmetric for the first phase (phase A) and the second phase (phase B) of the biphasic stimulus. Other pulse waveforms may be used. Exemplary parameters for a waveform are shown in FIG. 7, which illustrates a waveform used in an experiment described in more detail below, where the waveform had a pulse width of 200 μsec, an inter-pulse-interval of 50 μsec, a pulse amplitude of 250-1000 μA, and a frequency of 20 Hz.

The stimulator may generate a pulse train on a pair of electrodes. The pulses may be generated using a bipolar current source and can be capacitively isolated with >1 uF ceramic capacitors on both electrodes outputs. Compliance voltage can be set to as high as +/−18.8 volts.

Figure 8A:
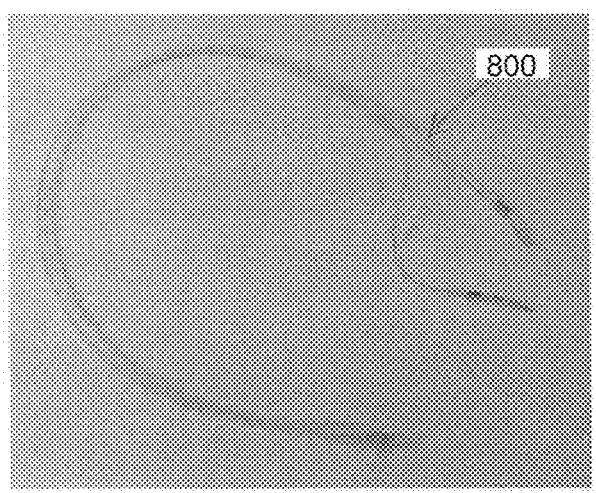
FIGS. 8A and 8B illustrate an embodiment of a nerve cuff lead that has been implanted around the vagus nerve.

The stimulator may use traditional electrode configurations, such as a cuff electrode 800 illustrated in FIG. 8A. Alternatively, the stimulator may be a microstimulator 810 as illustrated in FIG. 8C, which is further described in U.S. Pat. No. 8,612,002, which is herein incorporated by reference in its entirety.

As illustrated in the experimental example described below, appropriate NCAP stimulation of the vagus nerve can be used to limit the TNF inducibility of leukocytes in ex vivo blood by endotoxin, a reflection of the inflammatory responsiveness of the subject. Based on this data, a biphasic simulation at the parameters described above may successfully treat inflammatory disease, with progressively longer duration of anti-inflammatory effect with each successive stimulation.

Figure 8B:
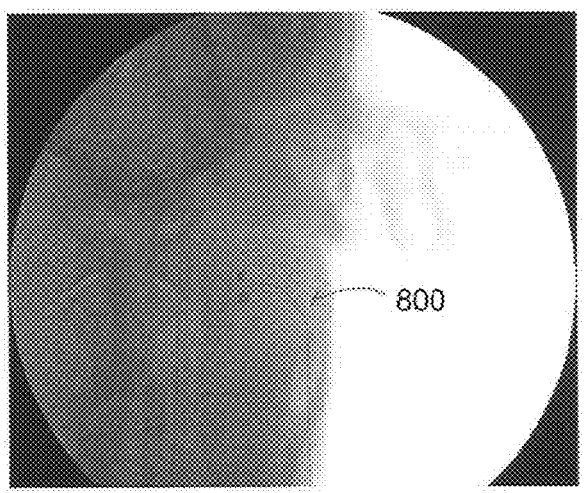
Figure 8C:
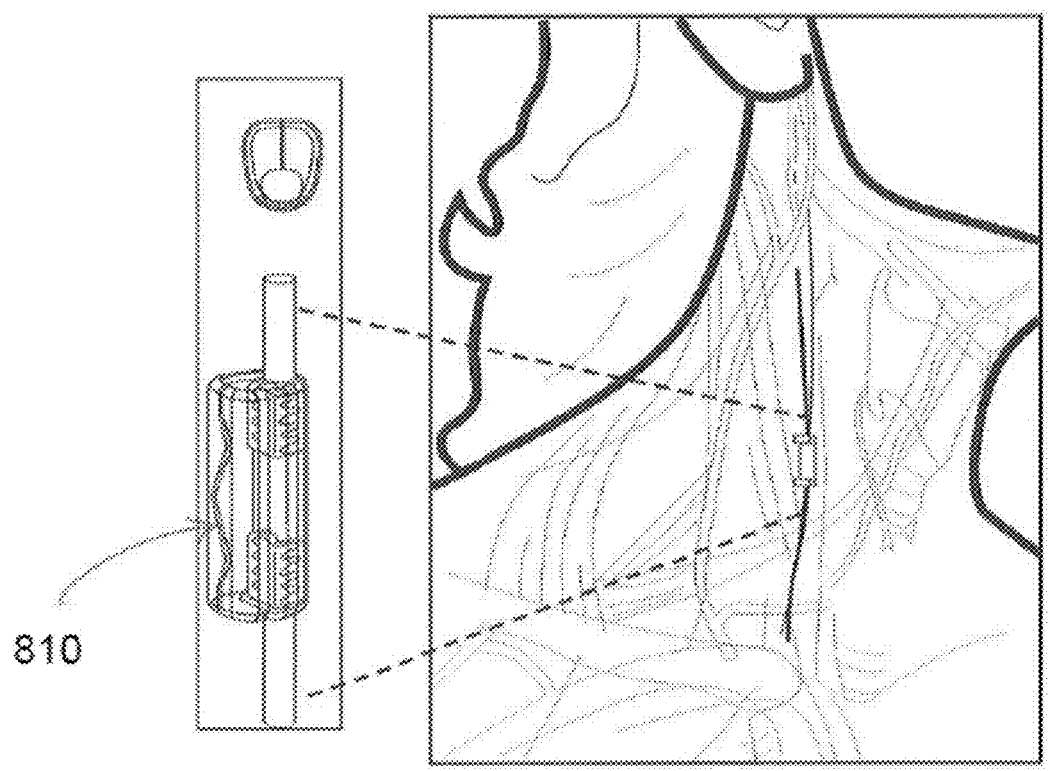
FIG. 8C illustrates an embodiment of a microstimulator.

FIGS. 8A and 8B illustrate one example in which progressively longer off-times were used to achieve a sustained inhibition of inflammation. Two canines (male, hound cross, about 1 years old) were anesthetized and nerve cuff electrodes 800 (Evergreen Medical, Minneapolis, MN) were placed around the cervical vagus nerve, as illustrated in FIGS. 8A and 8B. The lead body was externalized and protected under a jacket. Supra-threshold electrical pulses (250-1000 μA, 200 μS, 20 Hz, total of 600 stimuli per burst) were applied seven days apart. Blood was drawn about every three days, and the drawn blood was challenged with endotoxin ex vivo (0.1-0.5 ng/mL LPS) for four hours; the serum TNF levels were measured by ELISA to measure the effects on inflammatory cytokines.

Figure 9:
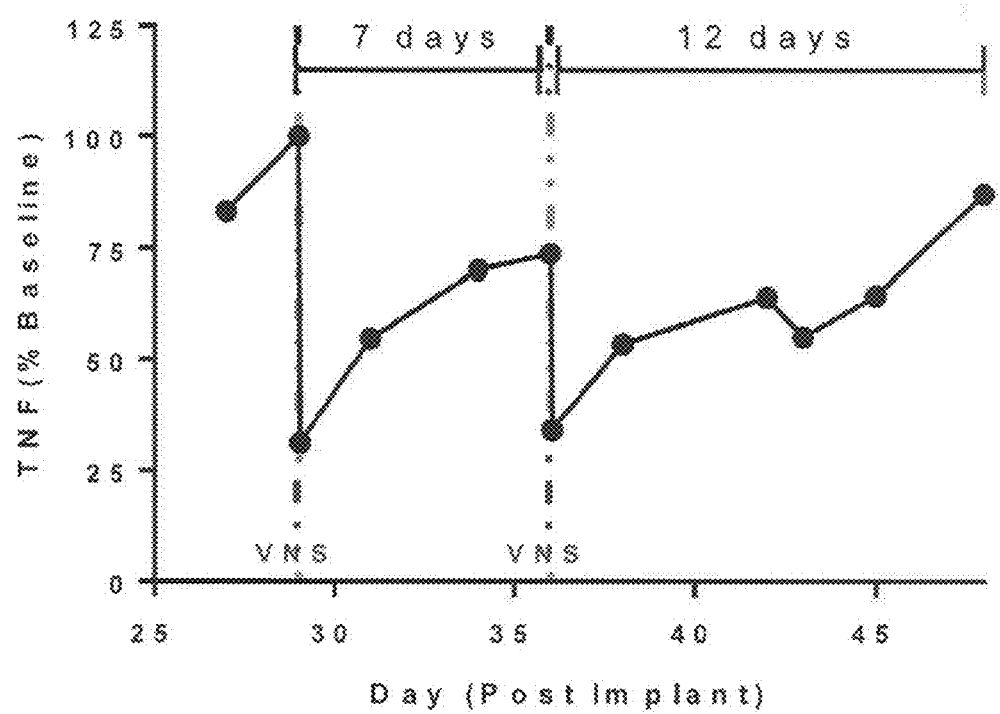
FIG. 9 presents canine data that shows that vagus nerve stimulation can achieve a long lasting anti-inflammatory effect and that the longevity of the effect can be increased.

As shown on FIG. 9, even a single 60 second stimulation of the vagus nerve resulted in a substantial suppression of TNF for at least 7 days. Thus, the initial effect was very long lasting. Additionally, when the canines were stimulated for a second time, the same second 60 second stimulation following upon the resulted in suppression of endotoxin-induced TNF for an even longer period of time, about 9-12 days. Thus, the anti-inflammatory effect was trainable to provide progressively increased longevity or duration of anti-inflammatory effect with each successive stimulation. Although the data in FIG. 9 are doses that each include a single burst of supra-threshold pulses (e.g., 600 per dose), the number of pulses may be different, and may be single-pulse. Although the onset of the effect of single pulse on markers for an anti-inflammatory (and/or inhibition of inflammation) response, the duration and extent of the effect is typically the same as that seen for multiple pulses (as discussed above for FIGS. 2-6).

These data illustrate an extremely persistent anti-inflammatory effect of vagus nerve stimulation on the blood of a large mammal with just a single stimulation dose. In this example, a single brief period of stimulation of the vagus nerve results in a surprisingly long-lasting effect (e.g., up to 7 days). Importantly, the persistence of this effect may be lengthened by training the inflammatory system through infrequent stimulations, potentially allowing for effective stimulations to be delivered weekly, monthly, every two months, quarterly or even annually. This data strongly suggests that stimulation may be provided extremely infrequently, with long (e.g., >48 h, >7 days) "silent" periods without stimulation applied. Such extremely low duty-cycle stimulation for treating IBD or rheumatoid arthritis and other diseases mediated by the inflammatory pathway may be particularly helpful in implantable systems, allowing extremely long battery life while having unexpectedly robust therapeutic benefits.

In general, these results suggest that the application of even a single brief stimulus (or burst of stimulus) of the vagus nerve may result in a substantial long term reduction in the effects of inflammation. Furthermore, these results suggest that the duration of the anti-inflammatory effect of the single stimulation may be increased by applying subsequent stimulations after a relatively lengthy period of time between stimulations. These results are surprising, given the prior arts tendency to stimulate for much longer times, and important for the design of future devices and methods. In particular, stimulation of the vagus nerve (or other portions of the inflammatory reflex) may be configured to apply extremely low duty-cycle stimulation. As mentioned briefly, this would allow for much smaller, lighter and more efficient implantable stimulation systems.

Figure 10:
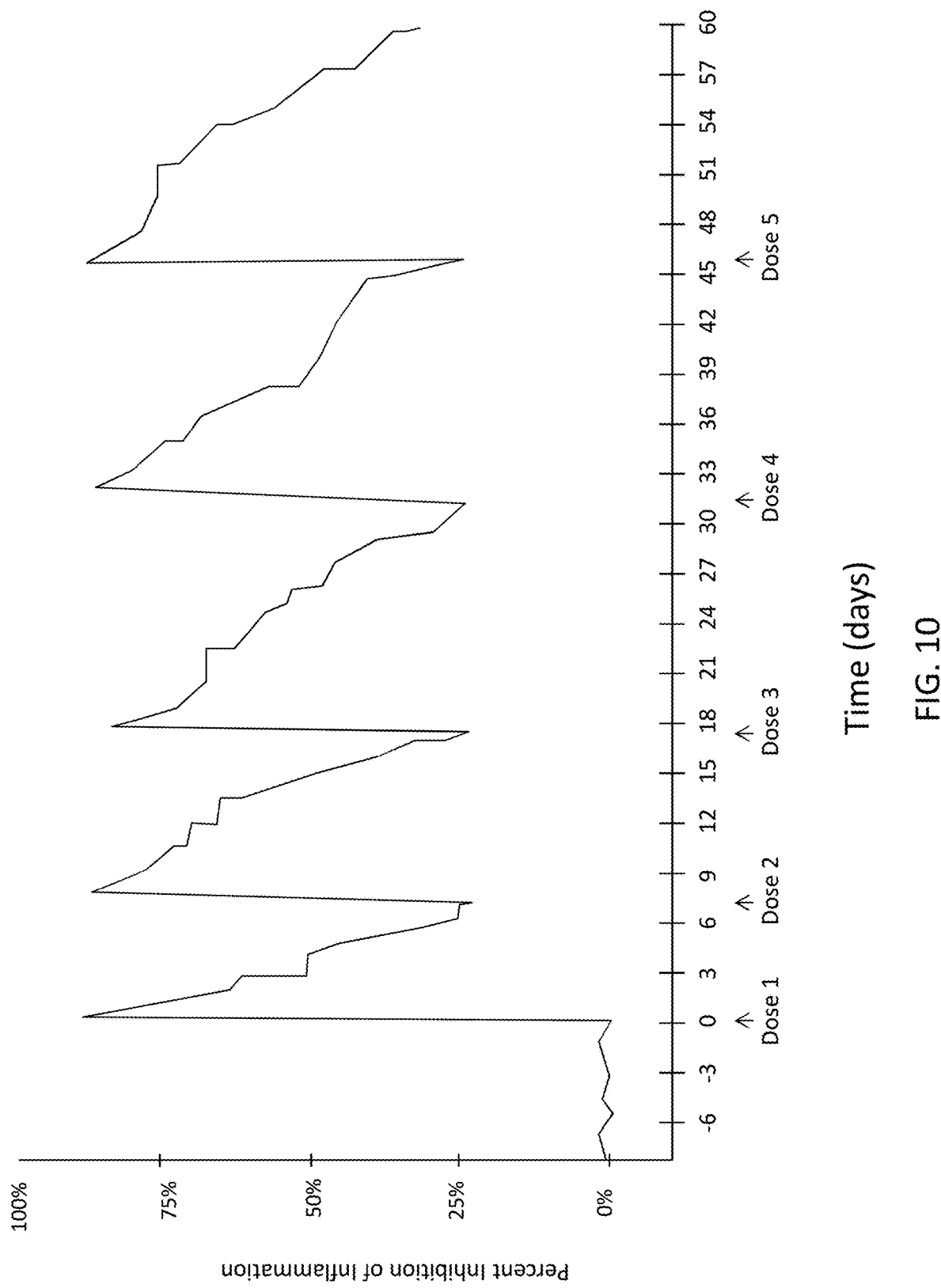
FIG. 10 is another example of vagus nerve stimulation with progressively longer off-times between extremely low duty-cycle does from a microstimulator on the vagus nerve. The percent inhibition of inflammation may be determined from the level of an analyte in the blood and/or vagus nerve activity, as described herein.

FIG. 10 illustrates a prophetic example of a dosing regimen that may maximize the progressively longer off times described above. In FIG. 10, a baseline of 0% inhibition of inflammation is shown prior to starting the stimulation from the implanted microstimulator. At t=0 (day 0), the first dose is applied. As mentioned, the first dose maybe a single supra-threshold pulse, or a single burst (e.g., 1 min, 2 min, 5 min) burst of supra-threshold stimulation, followed by an enforced off-time period, when stimulation is not applied. By day 7, the percent inhibition of inflammation has fallen back to nearly 25% inhibition. Thereafter, a second dose is applied (dose 2), driving inhibition back up. In this example, the inhibition following the second extremely low-duty cycle stimulation (does 2 may be the same or different as the electrical stimulation applied by dose 1) is longer-lasting that following the single dose, allowing a longer off-time period before the percent inhibition falls back to nearly 25% again at day 18 (approximately 10-11 days following dose 2). The third stimulation dose is applied, and the percent inhibition again takes even longer (e.g., 14-15 days) to fall back to nearly 25% inhibition of inflammation. Subsequent additional doses may be applied to sustain the inhibition of inflammation, as illustrated for doses 4 and 5 (or more); the off-time duration may continue to be reduced down to a maximum predetermined off time (e.g., 25 days, 28 days, 30 days, etc.).

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature. Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein. For example, as used herein, "about" and "approximately" can mean within 5, 10, 15, 20, 25, or 30 percent.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described What may be claimed is:

1. A system for treating chronic inflammation in a subject, the system comprising:
an implantable microstimulator configured to apply a stimulation dose to a vagus nerve, wherein the stimulation dose provides a single supra-threshold pulse or a burst of supra-threshold pulses, wherein a pulse width of the single supra-threshold pulse or each of the pulses of the burst of supra-threshold pulses is from 20 microsec to 2000 microsec, wherein each supra-threshold pulse is a biphasic pulse comprising a first pulse and a second pulse separated by a non-zero inter-pulse interval (IPI), and wherein the first pulse has an opposite pulse amplitude as the second pulse;
a nerve cuff comprising at least two electrodes configured to enclose the implantable microstimulator and to secure it around the vagus nerve; and
a controller adapted to adjust a dose regimen, wherein the dose regimen comprises a pulse amplitude, wherein the controller adjusts the pulse amplitude based on a monitored degree or level of inflammation, wherein each single supra-threshold pulse or burst of supra-threshold pulses results in long-lasting suppression of the monitored degree or level of inflammation and an off period, such that the controller adapts the dose regimen to set progressively delayed single supra-threshold pulses and progressively longer off periods, wherein the controller includes a bipolar current source to generate the biphasic pulse for the at least two electrodes,
wherein the dose regimen applied at the progressively delayed single supra-threshold pulses and the progressively longer off periods maintains an ongoing inhibition of the monitored degree or level of inflammation.

2. The system of claim 1, wherein the controller adjusts the dose regimen based on the level of inflammation based on an electrical activity of the vagus nerve.

3. The system of claim 1, wherein the off period is adjustable based on feedback from a sensor, wherein the controller is configured to measure an indicator of a level of inflammation based on an electrical activity of the vagus nerve.

4. The system of claim 1, wherein the off period is between 4 hours and 48 hours.

5. The system of claim 1, wherein the off period is between 8 hours and 48 hours.

6. The system of claim 1, wherein the single supra-threshold pulse or the burst of supra-threshold pulses has a pulse amplitude of less than 5 mA.

7. The system of claim 1, wherein the single supra-threshold pulse or the burst of supra-threshold pulses has a pulse amplitude of less than 3 mA.

8. The system of claim 1 wherein the single supra-threshold pulse or the burst of supra-threshold pulses has a pulse amplitude of less than 2 mA.

9. The system of claim 1, wherein the burst of supra-threshold pulses has a burst duration of less than 5 minutes.

10. The system of claim 1, wherein the burst of supra-threshold pulses comprises between 1 and 5 supra-threshold pulses.

11. The system of claim 1, wherein the IPI is at least 50 microseconds.

12. A method of treating chronic inflammation in a patient, the method comprising:
applying a dose regimen comprising a series of stimulation doses from a microstimulator to a vagus nerve through at least two electrodes, wherein the microstimulator is secured to the vagus nerve by a nerve cuff;
monitoring an indicator of a degree or level of inflammation; and
adjusting a pulse amplitude of the stimulation dose based on the monitored degree or level of inflammation,
wherein each stimulation dose comprises only a single supra-threshold stimulus pulse or a burst of supra-threshold pulses, wherein a pulse width of the single supra-threshold pulse or each of the pulses of the burst of supra-threshold pulses is from 20 microsec to 2000 microsec, and wherein each supra-threshold pulse is a biphasic pulse comprising a first pulse and a second pulse separated by a non-zero inter-pulse interval (IPI), and wherein the first pulse has an opposite pulse amplitude as the second pulse, wherein the biphasic pulse is generated by a bipolar current source coupled to the at least two electrodes,
wherein each single supra-threshold pulse or burst of supra-threshold pulses results in long-lasting suppression of the degree or level of inflammation and an off-period, thereby adapting the dose regimen to set progressively delayed single supra-threshold pulses and progressively longer off periods,
wherein the dose regimen applied at the progressively delayed single supra-threshold pulses and the progressively longer off periods maintains an ongoing inhibition of the monitored degree or level of inflammation.

13. The method of claim 12, wherein the off-time is at least 24 hours.

14. The method of claim 12, wherein the off-time is at least 48 hours.

15. The method of claim 12, wherein the single supra-threshold stimulus pulse or the burst of supra-threshold pulses has a pulse amplitude of less than 5 mA.

16. The method of claim 12, wherein the single supra-threshold stimulus pulse or the burst of supra-threshold pulses has a pulse amplitude of less than 3 mA.

17. The method of claim 12, wherein the single supra-threshold stimulus pulse or the burst of supra-threshold pulses has a pulse amplitude of less than 2 mA.

18. The method of claim 12, wherein the burst of supra-threshold pulses has a burst duration of less than 5 minutes.

19. The method of claim 11, wherein the method is a method of treating an intestinal disorder.

20. A method of inhibiting inflammation, the method comprising:
applying a dose regimen comprising a series of stimulation doses from a microstimulator through at least two electrodes to a vagus nerve of a patient, wherein the microstimulator is secured to the vagus nerve by a nerve cuff and further wherein each stimulation dose providing only a single supra-threshold stimulus pulse or a burst of supra-threshold pulses, wherein a pulse width of the single supra-threshold pulse or each of the pulses of the burst of supra-threshold pulses is from 20 microsec to 2000 microsec, and wherein each supra-threshold pulse is a biphasic pulse comprising a first pulse and a second pulse separated by a non-zero inter-pulse interval (IPI), wherein the first pulse has an opposite pulse amplitude as the second pulse, wherein the biphasic pulse for the at least two electrodes is generated by a bipolar current source, and wherein the bipolar current source is capacitively isolated with at least 1 microfarad (uF) ceramic capacitors coupled to each electrode;

monitoring the efficacy of the stimulation dose using a sensor of the microstimulator to determine a degree or level of inflammation; and adjusting a pulse amplitude between each stimulation dose based on the degree or level of inflammation;

wherein each single supra-threshold pulse or burst of supra-threshold pulses results in long-lasting suppression of the degree or level of inflammation and an off period, thereby adapting the dose regimen to set progressively delayed single supra-threshold pulses and progressively longer off periods, wherein the dose regimen applied at the progressively delayed single supra-threshold pulses and the progressively longer off periods maintains an ongoing inhibition of the monitored degree or level of inflammation.

21. The method of claim 20, wherein the method is a method of treating an intestinal disorder.

* * * * *